(12) United States Patent
Irie

(10) Patent No.: US 9,719,910 B2
(45) Date of Patent: Aug. 1, 2017

(54) PARTICLE DETECTING DEVICE

(71) Applicant: Azbil Corporation, Tokyo (JP)

(72) Inventor: Kanami Irie, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 67 days.

(21) Appl. No.: 14/723,920

(22) Filed: May 28, 2015

(65) Prior Publication Data

US 2015/0346074 A1 Dec. 3, 2015

(30) Foreign Application Priority Data

May 28, 2014 (JP) .................. 2014-110168

(51) Int. Cl.
| | |
|---|---|
| *G01N 15/14* | (2006.01) |
| *G01N 15/06* | (2006.01) |
| *G01N 15/00* | (2006.01) |
| *G01N 15/10* | (2006.01) |

(52) U.S. Cl.
CPC ......... *G01N 15/1404* (2013.01); *G01N 15/06* (2013.01); *G01N 15/1429* (2013.01); *G01N 15/1459* (2013.01); *G01N 2015/0046* (2013.01); *G01N 2015/0053* (2013.01); *G01N 2015/0693* (2013.01); *G01N 2015/1006* (2013.01)

(58) Field of Classification Search
CPC ........... G01N 15/1404; G01N 15/1429; G01N 15/1459; G01N 15/06; G01N 2015/0053; G01N 2015/0693; G01N 2015/1006; G01N 2015/0046
See application file for complete search history.

(56) References Cited

U.S. PATENT DOCUMENTS

| | | | | | |
|---|---|---|---|---|---|
| 3,787,122 | A | * | 1/1974 | Lepper, Jr. ............. | G01N 21/53 250/574 |
| 4,113,386 | A | * | 9/1978 | Lepper, Jr. ............. | G01N 21/53 250/574 |
| 5,452,084 | A | * | 9/1995 | Mitchell ................ | G01N 21/65 250/282 |
| 5,701,012 | A | | 12/1997 | Ho | |

(Continued)

FOREIGN PATENT DOCUMENTS

| | | |
|---|---|---|
| JP | 2008-225539 A | 9/2008 |
| JP | 2011-083214 A | 4/2011 |

OTHER PUBLICATIONS

N. Hasegawa, et al., Instantaneous Bioaerosol Detection Technology and Its Application, azbil Technical Review, 2-7, Yamatake Corporation, Dec. 2009.

*Primary Examiner* — Sang Nguyen
(74) *Attorney, Agent, or Firm* — Troutman Sanders LLP

(57) ABSTRACT

A particle detecting device includes: a chamber; an injection nozzle provided within the chamber; a discharge nozzle that is disposed within the chamber, opposing the injection nozzle; a detecting mechanism that illuminates a sample fluid that is sprayed from the injection nozzle and detects a particle included in the sample fluid; a pressurizing fluid pipe, connected to the chamber, for supplying a pressurizing fluid for pressurizing an interior of the chamber; and a rectifying member that rectifies the pressurizing fluid so that a flow speed distribution of a fluid between the injection nozzle and the discharge nozzle, rectified in an axial direction, is symmetrical in respect to the axial direction.

1 Claim, 23 Drawing Sheets

(56) References Cited

U.S. PATENT DOCUMENTS

| | | | |
|---|---|---|---|
| 8,358,411 B2* | 1/2013 | Babico | G01N 15/1459 |
| | | | 356/335 |
| 9,297,740 B2* | 3/2016 | Murakami | G01N 15/1404 |
| 2010/0165341 A1* | 7/2010 | Babico | G01J 3/02 |
| | | | 356/336 |
| 2013/0248693 A1* | 9/2013 | Buchanan, III | G01V 8/10 |
| | | | 250/222.2 |

\* cited by examiner

PARTICLE DETECTING DEVICE

CROSS REFERENCE TO RELATED APPLICATION

This application claims priority under 35 U.S.C. §119 to Japanese Patent Application No. 2014-110168, filed on May 28, 2014, the entire content of which being hereby incorporated herein by reference.

FIELD OF TECHNOLOGY

The present disclosure relates to a technology for evaluating an environment, relating to a particle detecting device.

BACKGROUND

In ordinary rooms or in clean rooms, such as bio clean rooms, airborne particles, including microorganisms, are detected and recorded using particle detecting devices. See, for example, U.S. Pat. No. 5,701,012, Japanese Unexamined Patent Application Publication Nos. 2008-225539 and 2011-083214, and N. Hasegawa, et al., *Instantaneous Bioaerosol Detection Technology and Its Application*, azbil Technical Review, 2-7, Yamatake Corporation, December 2009.

The optical particle detecting device comprises, for example, a chamber, an injection nozzle that is provided in the chamber, and a discharge nozzle that is provided in the chamber facing the injection nozzle. The particle detecting device draws in, for example, a fluid, such as air, within the room wherein the particle detecting device is placed, and sprays it, as a sample fluid, from the injection nozzle into the chamber. Additionally, the fluid within the chamber is discharged to the outside of the particle detecting device through the discharge nozzle. Furthermore, the particle detection device is provided with a detecting mechanism for illuminating, with a light beam, the sample fluid that is sprayed from the injection nozzle to detect particles included within the sample fluid. When there is a particle included within the sample fluid, a particle that is illuminated with light emits fluorescence or produces scattered light, enabling detection of the numbers, sizes, and the like, of particles included in the sample fluid.

Here, in the injection nozzle of the chamber, the cross-sectional area of the sample fluid that is introduced from the outside is constricted, increasing the speed of the flow, thus decreasing the surrounding pressure. Because of this, opposing flows are produced around the flow of the sample fluid that is formed between the injection nozzle and the discharge nozzle. Furthermore, there are cases wherein the discharge of the fluid from the discharge nozzle does not go smoothly because of the drop in pressure within the chamber. When opposing flows are produced within the chamber or when there is a pressure drop within the chamber, particles may remain stagnant within the chamber. When particles remain stagnant within the chamber, then the detecting mechanism may count the same particle multiple times, which may make it difficult to detect accurately the number of particles included in a unit volume of the fluid.

In this regard, a method has been proposed wherein the interior of the chamber is pressurized through supplying a pressurizing fluid, from which particles have been eliminated, into the chamber from an opening other than the injection nozzle. See, for example, U.S. Patent Application Publication No. 2013/0248693.

However, the present inventor discovered that there may be cases wherein the flow of the pressurizing fluid, injected from an opening other than the injection nozzle, may disrupt the flow of the sample fluid between the injection nozzle and the discharge nozzle. When the flow of the sample fluid between the injection nozzle and the discharge nozzle is disrupted, the particles included in the sample fluid that should be discharged from the discharge nozzle may remain stagnant within the chamber. If particles that remain stagnant within the chamber are detected multiple times, then there may be an incorrect evaluation of the number of particles included within the sample fluid. Moreover, the particles that remain stagnant within the chamber may cause contamination. Given this, an aspect of the present invention is to provide a particle detecting device wherein there is less of a tendency for particles to remain stagnant internally.

SUMMARY

Such an aspect of the present disclosure provides a particle detecting device including:
a chamber;
an injection nozzle provided within the chamber;
a discharge nozzle that is disposed within the chamber, opposing the injection nozzle;
a detecting mechanism for illuminating the sample fluid that is sprayed from the injection nozzle to detect a particle included in the sample fluid;
a pressurizing fluid pipe, connected to the chamber, for supplying a pressurizing fluid for pressurizing the interior of the chamber; and
a rectifying member for rectifying the pressurizing fluid so that the flow speed distribution of the fluid between the injection nozzle and the discharge nozzle, rectified in the axial direction, will be symmetrical in respect to the axial direction.

An aspect of the present disclosure provides a particle detecting device including:
a chamber;
an injection nozzle provided within the chamber;
a discharge nozzle that is disposed within the chamber, opposing the injection nozzle;
a detecting mechanism for illuminating the sample fluid that is sprayed from the injection nozzle to detect a particle included in the sample fluid;
a pressurizing fluid pipe, connected to the chamber, for supplying a pressurizing fluid for pressurizing the interior of the chamber; and
a rectifying member for rectifying the flow of the pressurizing fluid;
wherein:
the rectifying member is a part of the pressurizing fluid pipe that protrudes into the chamber, and is provided with an opening in a side wall of the part of the pressurizing fluid pipe that protrudes into the chamber. The opening in the sidewall of the part of the pressurizing fluid pipe that protrudes into the chamber may be provided multiply. Meshes, filters, or porous members may be provided in the openings. An end of the pressurizing fluid pipe that protrudes into the chamber may be closed.

An aspect of the present disclosure provides a particle detecting device including:
a chamber;
an injection nozzle provided within the chamber;
a discharge nozzle that is disposed within the chamber, opposing the injection nozzle;
a detecting mechanism for illuminating the sample fluid that is sprayed from the injection nozzle to detect a particle included in the sample fluid;

a pressurizing fluid pipe, connected to the chamber, for supplying a pressurizing fluid for pressurizing the interior of the chamber; and a rectifying member for rectifying the flow of the pressurizing fluid;

wherein:

the rectifying member is a plate that is disposed facing an opening of the pressurizing fluid pipe that is connected to the chamber. At least a portion of the detecting mechanism may be provided in the rectifying member.

An aspect of the present disclosure provides a particle detecting device including:

a chamber;

an injection nozzle provided within the chamber;

a discharge nozzle that is disposed within the chamber, opposing the injection nozzle;

a detecting mechanism for illuminating the sample fluid that is sprayed from the injection nozzle to detect a particle included in the sample fluid;

a pressurizing fluid pipe, connected to the chamber, for supplying a pressurizing fluid for pressurizing the interior of the chamber; and a rectifying member for rectifying the flow of the pressurizing fluid;

wherein:

the rectifying member is a mesh that is disposed facing an opening of the pressurizing fluid pipe that is connected to the chamber. At least a portion of the detecting mechanism may be provided in the rectifying member.

An aspect of the present disclosure provides a particle detecting device including:

a chamber;

an injection nozzle provided within the chamber;

a discharge nozzle that is disposed within the chamber, opposing the injection nozzle;

a detecting mechanism for illuminating the sample fluid that is sprayed from the injection nozzle to detect a particle included in the sample fluid;

a pressurizing fluid pipe, connected to the chamber, for supplying a pressurizing fluid for pressurizing the interior of the chamber; and a rectifying member for rectifying the flow of the pressurizing fluid;

wherein:

the rectifying member is a filter that is disposed facing an opening of the pressurizing fluid pipe that is connected to the chamber. At least a portion of the detecting mechanism may be provided in the rectifying member.

An aspect of the present disclosure provides a particle detecting device comprising:

a chamber;

an injection nozzle provided within the chamber;

a discharge nozzle that is disposed within the chamber, opposing the injection nozzle;

a detecting mechanism for illuminating the sample fluid that is sprayed from the injection nozzle to detect a particle included in the sample fluid;

a pressurizing fluid pipe, connected to the chamber, for supplying a pressurizing fluid for pressurizing the interior of the chamber; and a rectifying member for rectifying the flow of the pressurizing fluid;

wherein:

the rectifying member is a porous member that is disposed facing an opening of the pressurizing fluid pipe that is connected to the chamber. At least a portion of the detecting mechanism may be provided in the rectifying member.

An aspect of the present disclosure provides a particle detecting device comprising:

a chamber;

an injection nozzle provided within the chamber;

a discharge nozzle that is disposed within the chamber, opposing the injection nozzle;

a detecting mechanism for illuminating the sample fluid that is sprayed from the injection nozzle to detect a particle included in the sample fluid;

a pressurizing fluid pipe, connected to the chamber, for supplying a pressurizing fluid for pressurizing the interior of the chamber; and a rectifying member for rectifying the flow of the pressurizing fluid;

wherein:

the rectifying member is a tubular member for covering at least between the injection nozzle and the discharge nozzle. At least a portion of the tubular member may be made from, for example, a mesh, a filter, or a porous material. Moreover, at least a portion of the detecting mechanism may be provided in the tubular member.

An aspect of the present disclosure provides a particle detecting device comprising:

a chamber;

an injection nozzle provided within the chamber;

a discharge nozzle that is disposed within the chamber, opposing the injection nozzle;

a detecting mechanism for illuminating the sample fluid that is sprayed from the injection nozzle to detect a particle included in the sample fluid;

a pressurizing fluid pipe, connected to the chamber, for supplying a pressurizing fluid for pressurizing the interior of the chamber; and a rectifying member for rectifying the flow of the pressurizing fluid;

wherein:

the rectifying member is a second chamber that is disposed within the first chamber, wherein the injection nozzle and the discharge nozzle face each other within the second chamber. At least a portion of the second chamber may be made from, for example, a mesh, a filter, or a porous material. At least a portion of the detecting mechanism may be provided in the second chamber.

A particle detecting device according to an aspect set forth above may further comprise: a pressurizing fluid filter for eliminating particles from the pressurizing fluid that is supplied to the chamber.

The present invention can provide a particle detecting device wherein there is less of a tendency for particles to remain stagnant therein.

BRIEF DESCRIPTIONS OF THE DRAWINGS

DETAILED DESCRIPTION

Examples of the present disclosure will be described below. In the descriptions of the drawings below, identical or similar parts are expressed by identical or similar codes. Note that the diagrams are schematic. Consequently, specific measurements should be evaluated in light of the descriptions below. Furthermore, even within these drawings there may, of course, be portions having differing dimensional relationships and proportions.

EXAMPLE

Figure 1:
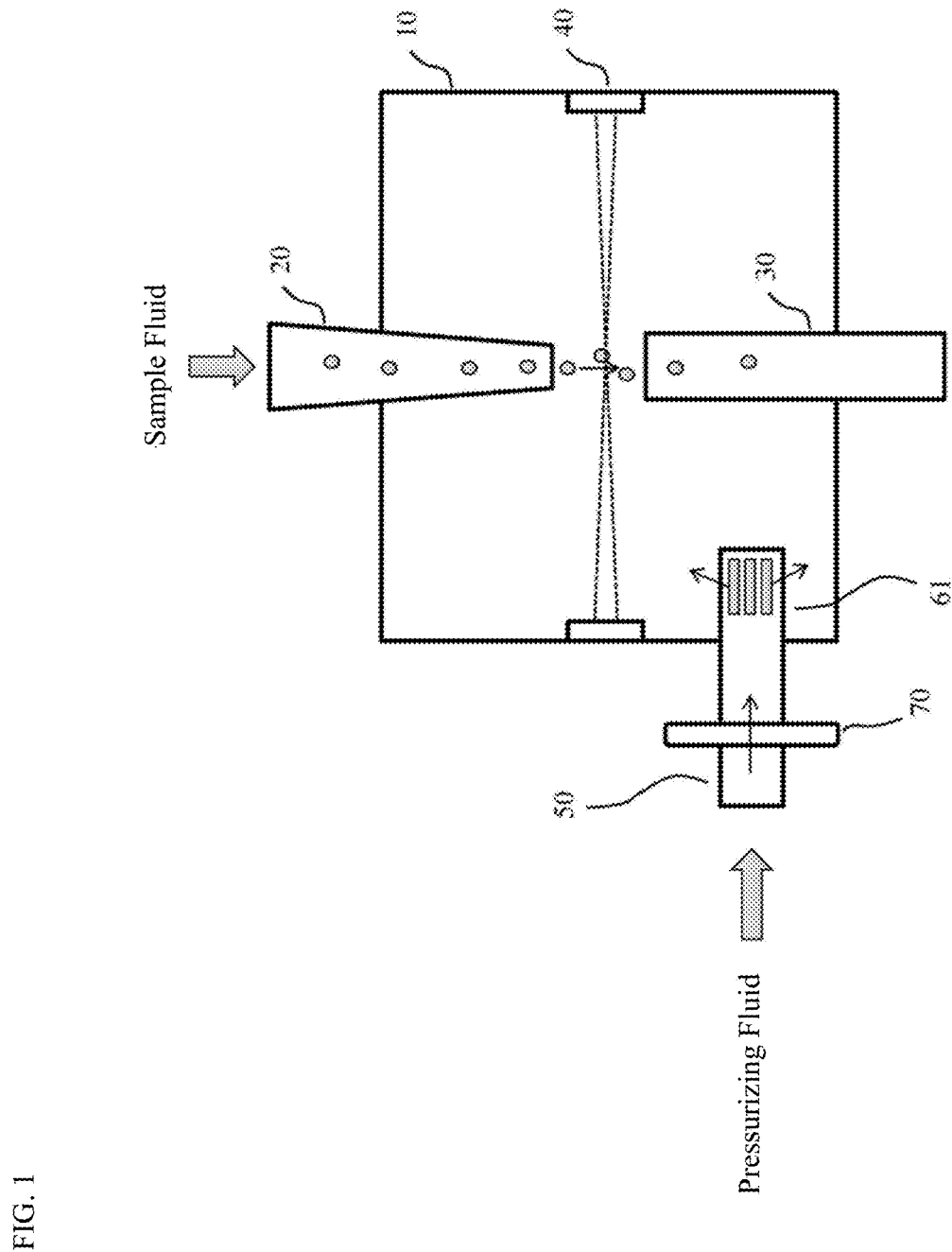
FIG. 1 is a schematic diagram of a particle detecting device as set forth in Example according to the present disclosure.

A particle detecting device according to Example, as illustrated in FIG. 1, comprises: a chamber 10; an injection nozzle 20 that is provided within the chamber 10; a discharge nozzle 30 that is provided within the chamber 10, facing the injection nozzle 20; a detecting mechanism 40 for illuminating with light the sample fluid that is sprayed from the injection nozzle 20, to detect particles included within the sample fluid; a pressurizing fluid pipe 50, connected to the chamber 10, for supplying pressurizing fluid for pressurizing the chamber 10; and a rectifying member 61 for rectifying the pressurizing fluid so that the flow speed distribution of the fluid, rectified in the axial direction, between the injection nozzle 20 and the discharge nozzle 30, will be symmetrical in respect to the axial direction. Here the "fluid" may be a gas or a liquid.

The shape and material of the chamber 10 are arbitrary. However, preferably the chamber 10 is able to withstand pressure. A sample injecting path, provided with a pipe made from metal, resin, or the like, is connected to the injection nozzle 20. Moreover, a discharge path, provided with a pipe made from metal, resin, or the like, for example, is connected to the discharge nozzle 30. Moreover, a discharge blower pump, as a discharge blower, for example, is provided in the discharge path.

The sample fluid that is drawn from the outside of the particle detecting device by the discharge blower pump is sprayed through the sample injection path and the injection nozzle 20 into the chamber 10. The fluid that is blown into the chamber 10 is discharged from the chamber 10 through the discharge nozzle 30 that is provided opposing the injection nozzle 20, and then passes through the discharge flow path, to be discharged to the outside of the particle detecting device.

The detecting mechanism 40 comprises a light source for illuminating the flow of the sample fluid, such as air, or the like, that is formed between the injection nozzle 20 and the discharge nozzle 30, and a photodetecting element for detecting scattered light produced by the particles in the sample fluid, to detect the number of particles included. Conversely, the detecting mechanism 40 is provided with a photodetecting element for detecting fluorescence that is produced by a particle included in the sample fluid. Moreover, the detecting mechanism 40 can calculate the density of particles in the sample fluid through dividing the number of particles detected per unit time by the volume of sample fluid that is drawn in from the outside of the particle detecting device.

Here "particles" includes biological substances such as microorganisms, chemical substances, and dust such as dirt, grime, etc. Examples of microorganisms include bacteria and fungi. Gram-negative bacteria and Gram-positive bacteria can be listed as examples of bacteria. *Escherichia coli*, for example, can be listed as an example of a Gram-negative bacterium. *Staphylococcus epidermidis, Bacillus atrophaeus, Micrococcus lylae,* and *Corynebacterium afermentans* can be listed as examples of Gram-positive bacteria. *Aspergillus* species such as *Aspergillus niger* can be listed as examples of fungi. However, the microorganisms are not limited to these examples.

When a fluorescent particle, such as a microorganism, is included, the particle, when illuminated with light, will emit fluorescent light. For example, riboflavin, flavin nucleotides (FMN), flavin adenine dinucleotide (FAD), nicotinamide adenine dinucleotide phosphate (NAD(P)H), pyridoxamine, pyridoxal phosphate (pyridoxal-5'-phosphate), pyridoxine, tryptophan, tyrosine, phenylalanine, and the like, that are included in the microorganisms will produce fluorescence.

In the injection nozzle 20 of the chamber 10, the cross-sectional area of the sample fluid is constricted, increasing the speed of the flow, and thus decreasing the surrounding pressure. Here when no pressurizing fluid is supplied into the chamber 10 through the pressurizing fluid pipe 50, the pressure within the chamber 10 may become lower than the pressure of the discharge nozzle 30. In this case, particles included within the sample fluid will be dispersed within the chamber 10, wherein the pressure is less than that of the discharge nozzle 30. When particles are dispersed and remain stagnant within the chamber 10, then the detecting mechanism 40 may count the same particle multiple times, which may make it difficult to detect accurately the number of particles included in a unit volume of the fluid.

In contrast, in the particle detecting device according to the Example, the state of the fluid within the chamber 10 is adjusted by increasing the pressure within the chamber 10, or through rectifying the flow of the fluid in the chamber 10, through providing a pressurizing fluid, from which particles have been removed, into the chamber 10 through a pressurizing fluid pipe 50 that is connected to the chamber 10. As a result, the pressure within the chamber 10 increases following the pressure within the injection nozzle 20, making it possible to prevent the pressure within the chamber 10 from being lower than the pressure within the discharge nozzle 30. Because of this, it is possible to cause the sample fluid that is sprayed from the injection nozzle 20 to proceed smoothly into the discharge nozzle 30 wherein the pressure is low. A pressurizing fluid filter 70, for example, for eliminating particles from the pressurizing fluid, is provided in the pressurizing fluid pipe 50. As a pressurizing fluid filter 70, a HEPA filter (a High Efficiency Particulate Air Filter), or the like, may be used.

Figure 2:
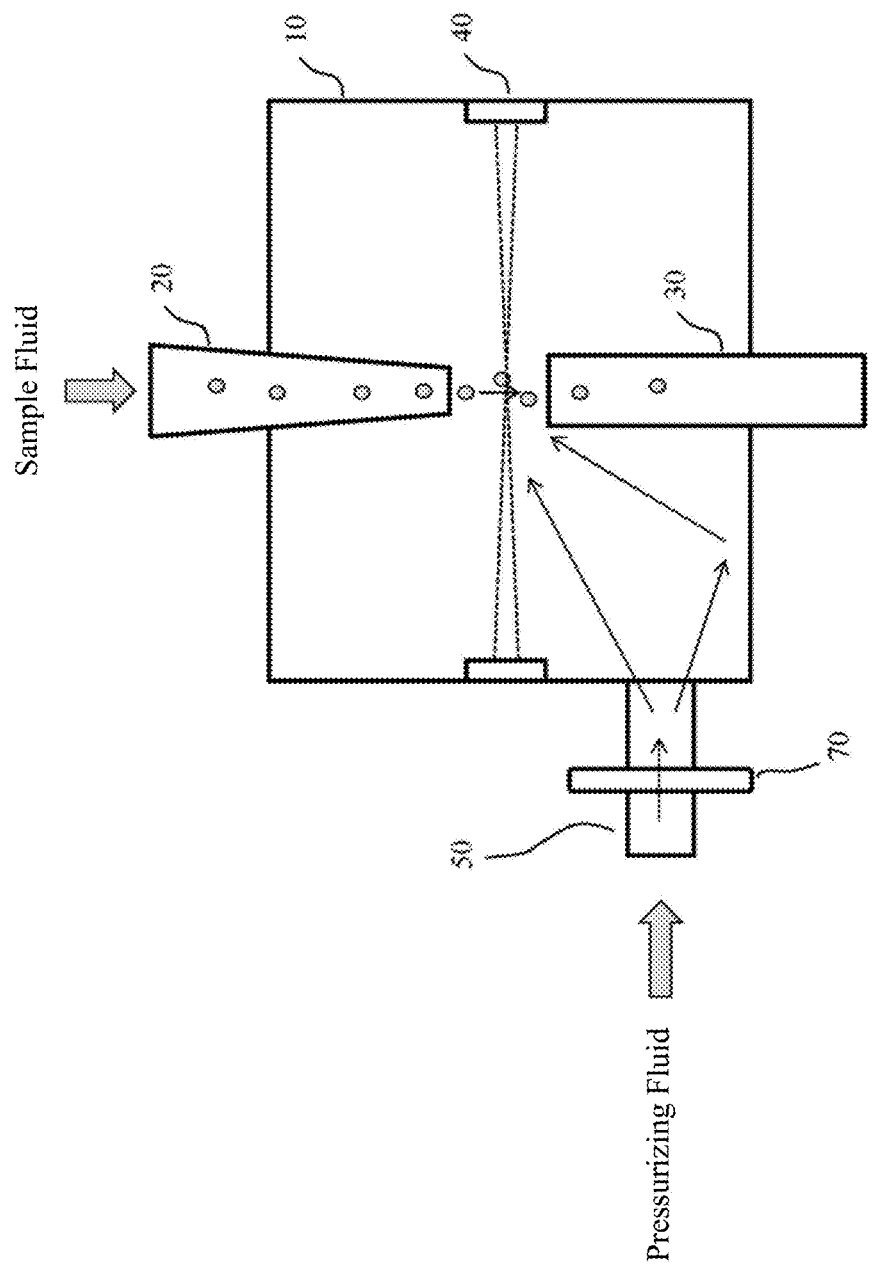
FIG. 2 is a schematic diagram of a particle detecting device as set forth in a reference example of the Example according to the present disclosure.

However, when, as illustrated in the reference example in FIG. 2, no rectifying member is provided and there is no blockage whatsoever to the flow of the pressurizing fluid, a large asymmetrical flow will be produced by the pressurizing fluid within the chamber 10, causing the flow speed distribution of the fluid between the injection nozzle 20 and the discharge nozzle 30, which has been rectified in the axial direction, to cease to be symmetrical in respect to the axial direction, disrupting the flow speed distribution. When the flow of the sample fluid between the injection nozzle 20 and discharge nozzle 30 is disrupted, the particles included in the sample fluid, which should be discharged from the discharge nozzle 30, may remain stagnant within the chamber 10.

Figure 3:
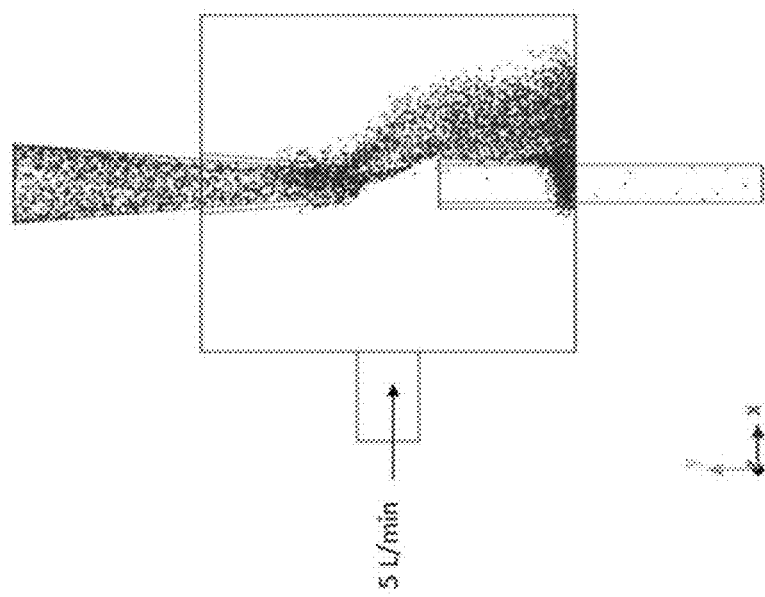
FIG. 3 is a simulation result illustrating the distribution of particles within the chamber of the particle detecting device in a case wherein no flow rectifying member is provided.
Figure 4:
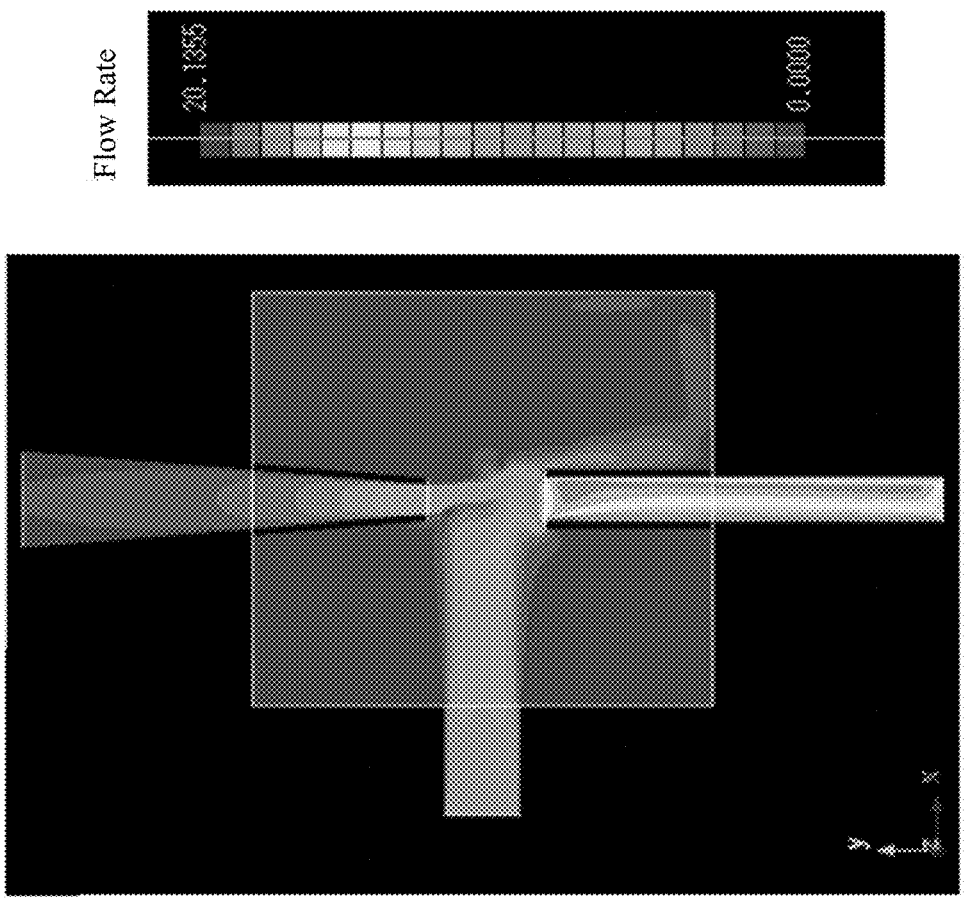
FIG. 4 is a simulation result illustrating the distribution of flow speeds within the chamber of the particle detecting device in a case wherein no flow rectifying member is provided.
Figure 5:
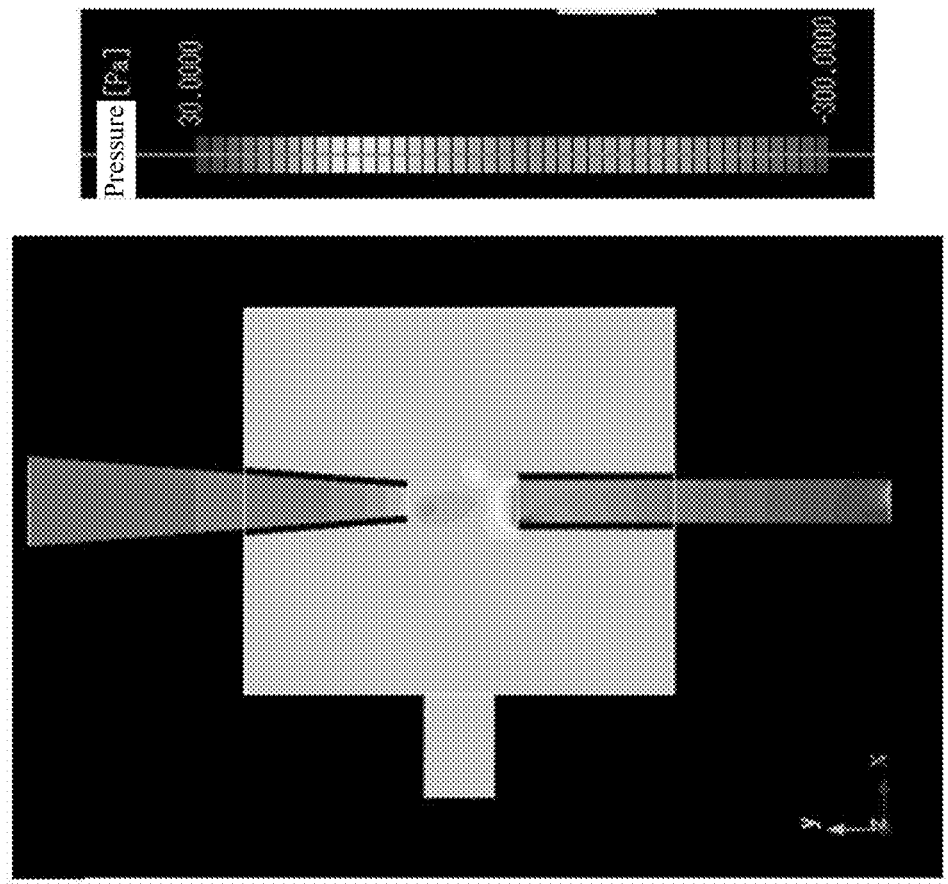
FIG. 5 is a simulation result illustrating the distribution of pressures within the chamber of the particle detecting device in a case wherein no flow rectifying member is provided.

FIG. 3 illustrates the distribution of particles within the chamber of the particle detecting device when no rectifying member is provided, FIG. 4 illustrates the distribution of the flow speeds, and FIG. 5 illustrates the distribution of the pressures. The distributions illustrated in FIG. 3 through FIG. 5 are the results of simulations. As illustrated in FIG. 3, the particles are not discharged from the discharge nozzle because no rectifying member is provided. Moreover, as illustrated in FIG. 4, the pressurizing fluid arrives between the injection nozzle and the discharge nozzle while still at a high flow speed. Moreover, as illustrated in FIG. 5, the pressure distribution is asymmetrical in the vicinity of between the injection nozzle and the discharge nozzle.

In contrast, in the particle detecting device according to the Example, as illustrated in FIG. 1, a rectifying member 61, for rectifying the pressurizing fluid, is provided so as to prevent the occurrence of the large asymmetrical flow within the chamber 10, so that the distribution of the flow speeds of the fluid between the injection nozzle 20 and the discharge nozzle 30, which have been rectified in the axial direction, will be symmetrical in respect to the axial direction. In the Example, the rectifying member 61 is a part of the pressurizing fluid pipe 50 that protrudes into the chamber 10.

Figure 6:
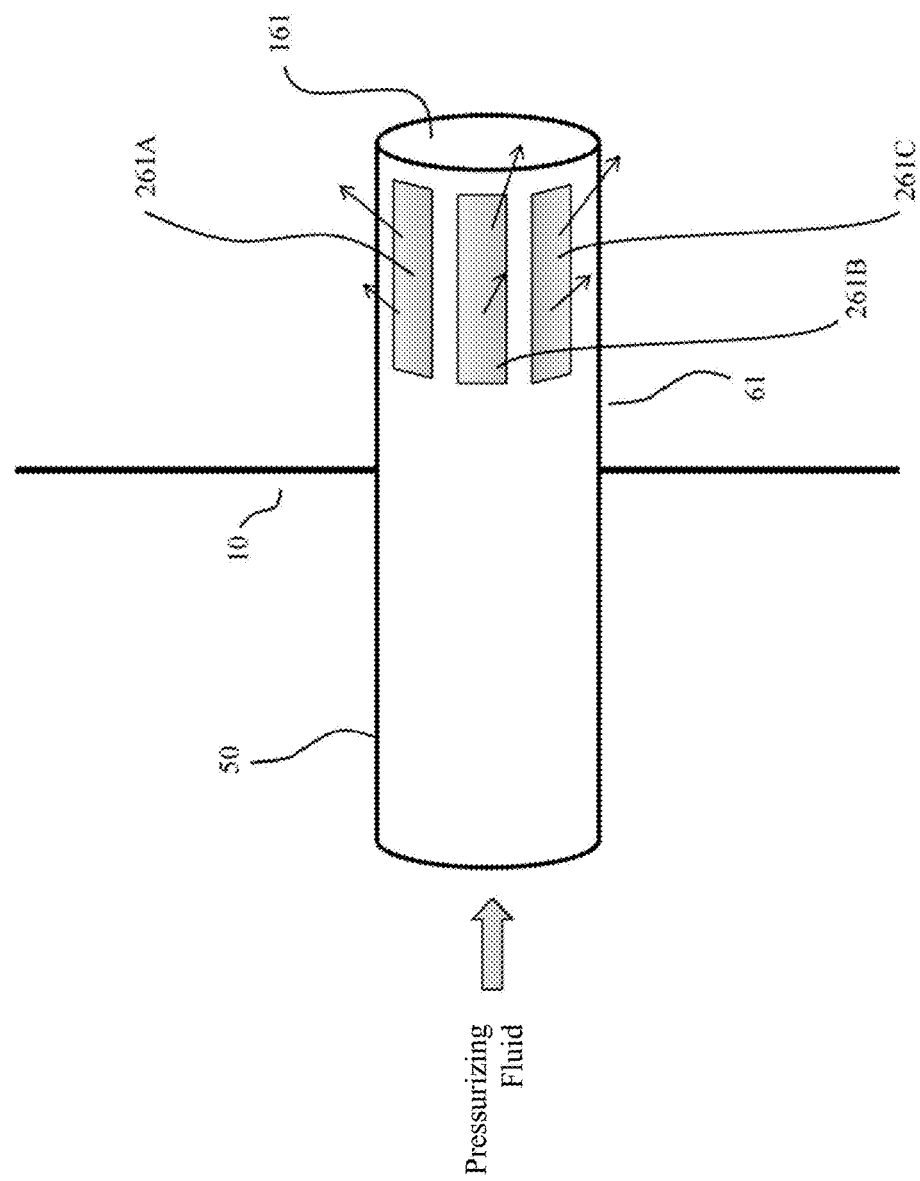
FIG. 6 is a schematic diagram of a flow rectifying member in the particle detecting device as set forth in the Example according to the present disclosure.
Figure 7:
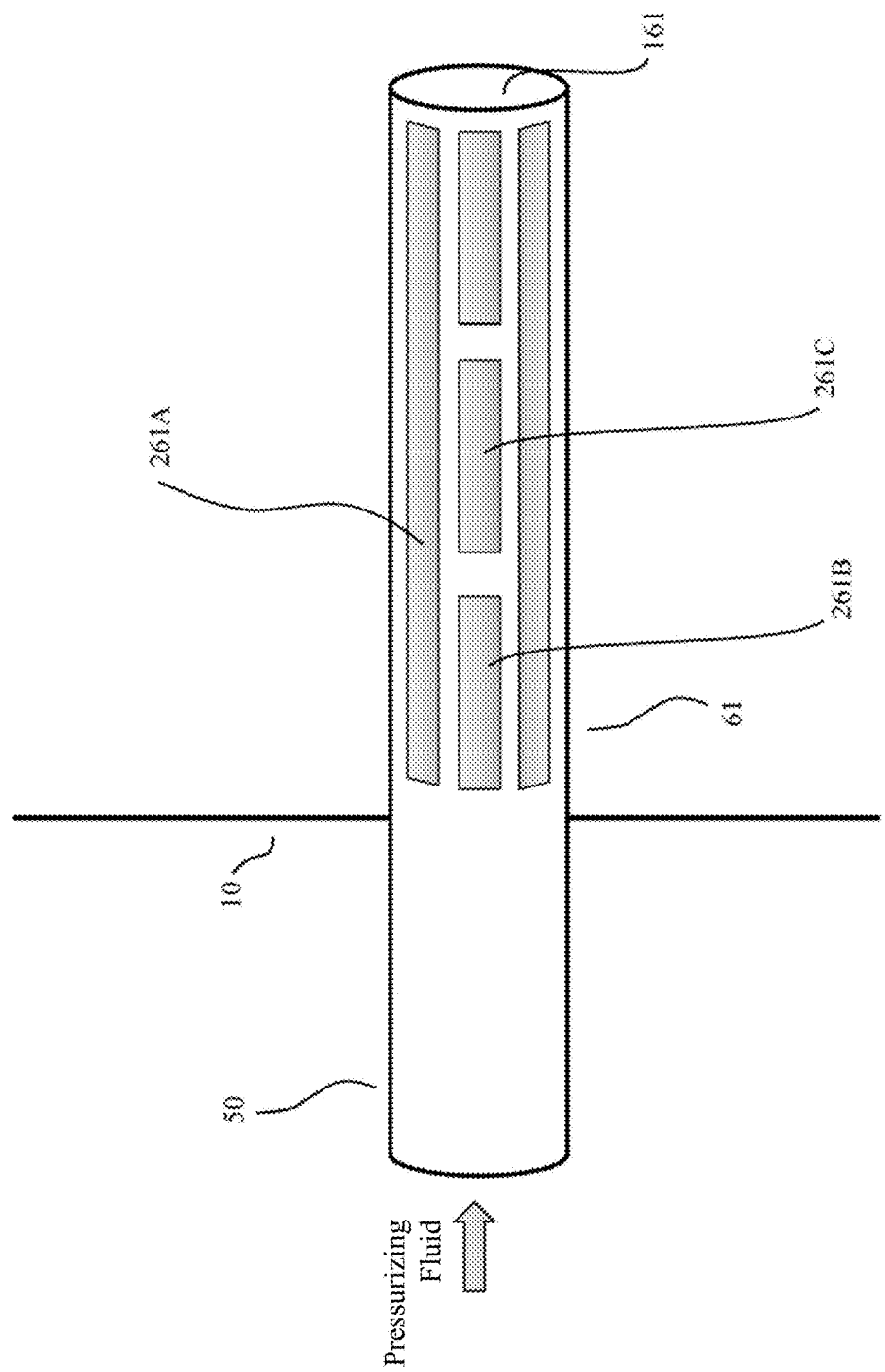
FIG. 7 is a schematic diagram of a flow rectifying member in the particle detecting device as set forth in the Example according to the present disclosure.

As illustrated in FIG. 6 and FIG. 7, openings 261A, 261B, and 261C are provided in the sidewalls of the part of the pressurizing fluid pipe 50 that protrudes into the chamber 10. There may be a single opening or multiple openings. Moreover, the shapes of the openings 261A, 261B, and 261C are, for example, slits, but there is no limitation thereto. Meshes, filters, or porous members may be provided in the openings 261A, 261B, and 261C. Preferably the materials for the meshes, filters, or porous members are dust-free materials. For example, for the filter a HEPA filter, an ULPA filter (Ultra Low Penetration Air Filter), a nylon net, or the like, may be used. Metal, plastic, glass, or the like, may be used as the material for the meshes or porous members.

The pressurizing fluid flows into the chamber 10 from the openings 261A, 261B, and 261C. The greater the total area of the openings 261A, 261B, and 261C, the more uniform the disbursement of the pressure of the pressurizing fluid within the chamber 10 can be. Because of this, the part of the pressurizing fluid pipe 50 that protrudes into the chamber 10 may be made long, for example, to provide a large surface area for the protruding portion, to thereby secure a large total area for the openings 261A, 261B, and 261C.

The sidewall of the part of the pressurizing fluid pipe 50 that protrudes into the chamber 10 is essentially perpendicular to the direction of flow of the sample fluid between the injection nozzle 20 and the discharge nozzle 30. The end of the pressurizing fluid pipe 50 that protrudes into the chamber 10 is closed by a closed face 161. The closed face 161 is essentially parallel to the direction of flow of the sample fluid between the injection nozzle 20 and the discharge nozzle 30. This makes it possible to prevent the pressurizing fluid that flows into the chamber 10 from the openings 261A, 261B, and 261C from disrupting asymmetrically the flow speed distribution of the fluid between the injection nozzle 20 and the discharge nozzle 30 that has been rectified in the axial direction.

ANOTHER EXAMPLE

Figure 8:
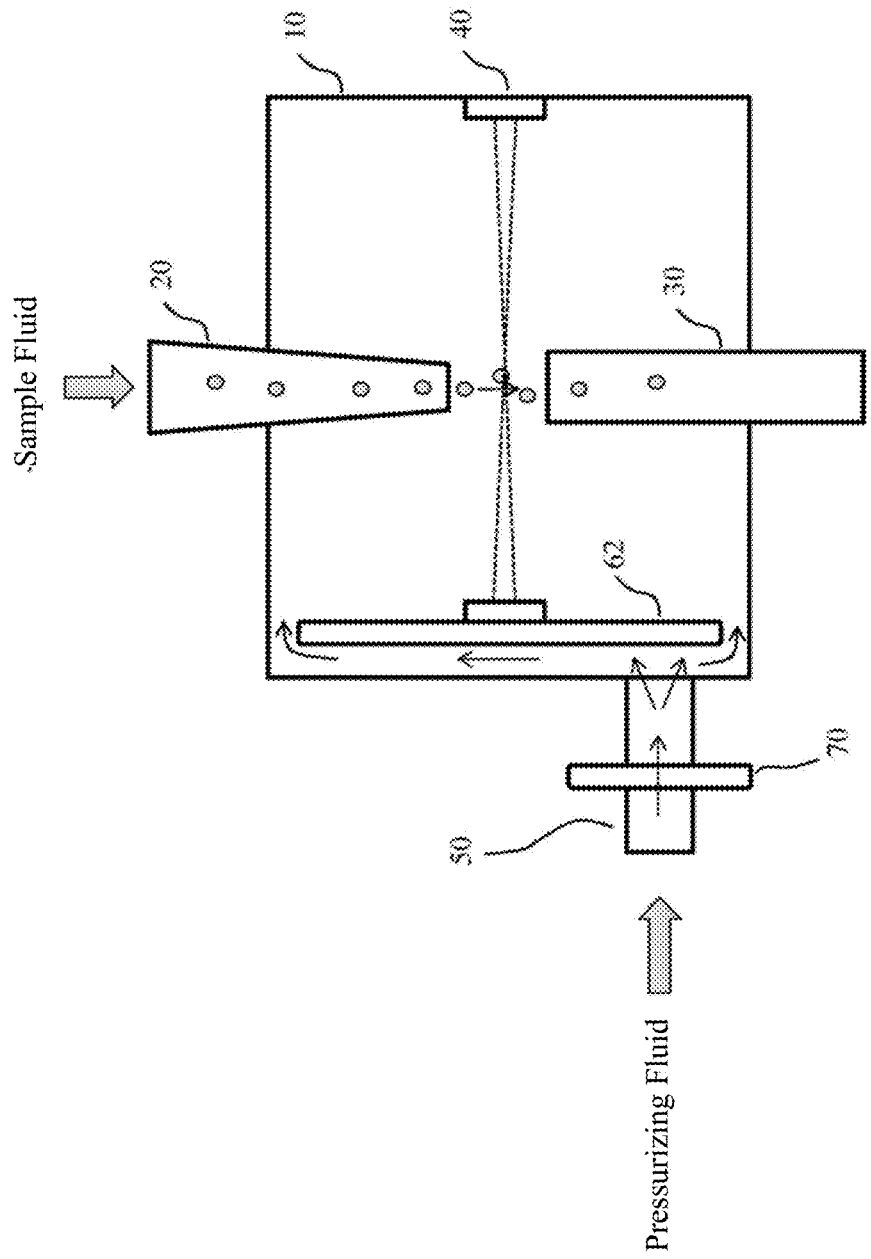
FIG. 8 is a schematic diagram of a particle detecting device as set forth in Another Example according to the present disclosure.

In a particle detecting device according to Another Example, as illustrated in FIG. 8, the pressurizing fluid pipe 50 does not protrude into the chamber 10, but rather the end of the pressurizing fluid pipe 50 is connected to an outer diameter portion of an opening that is provided in a side wall of the chamber 10. The pressurizing fluid that is supplied from the pressurizing fluid pipe 50 is supplied into the chamber 10 from the opening that is provided in the sidewall of the chamber 10. For example, the sidewall of the chamber 10 wherein the opening through which the pressurizing fluid passes is provided is essentially parallel to the direction of flow of the sample fluid between the injection nozzle 20 and the discharge nozzle 30.

Figure 9:
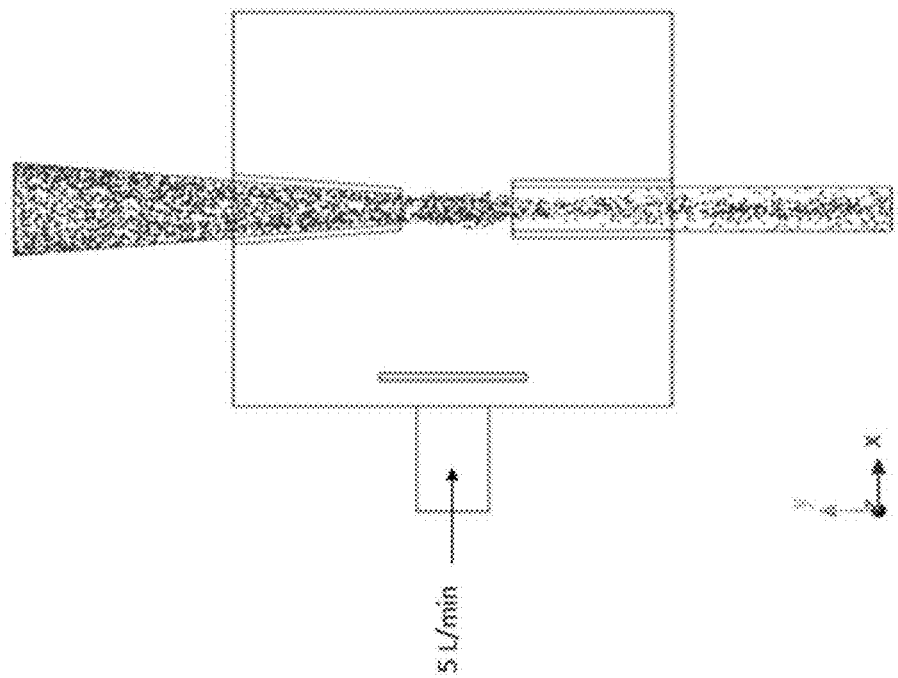
FIG. 9 is a simulation result illustrating the distribution of particles within the chamber of the particle detecting device in a case wherein a flow rectifying member is provided.
Figure 10:
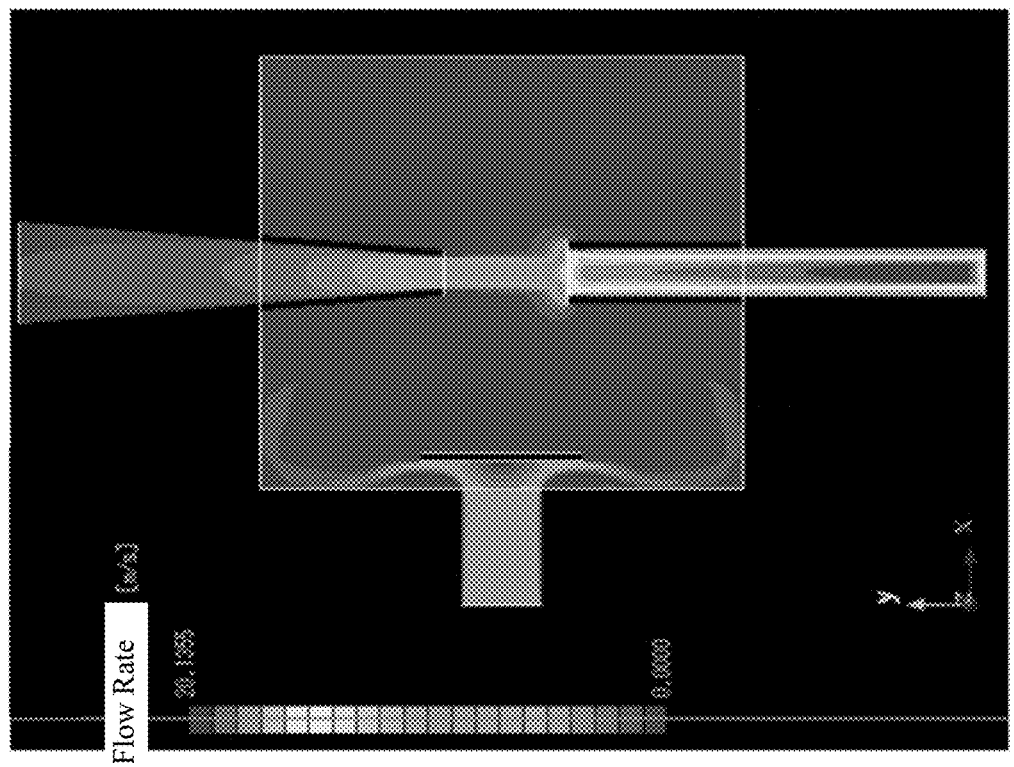
FIG. 10 is a simulation result illustrating the distribution of flow speeds within the chamber of the particle detecting device in a case wherein a flow rectifying member is provided.
Figure 11:
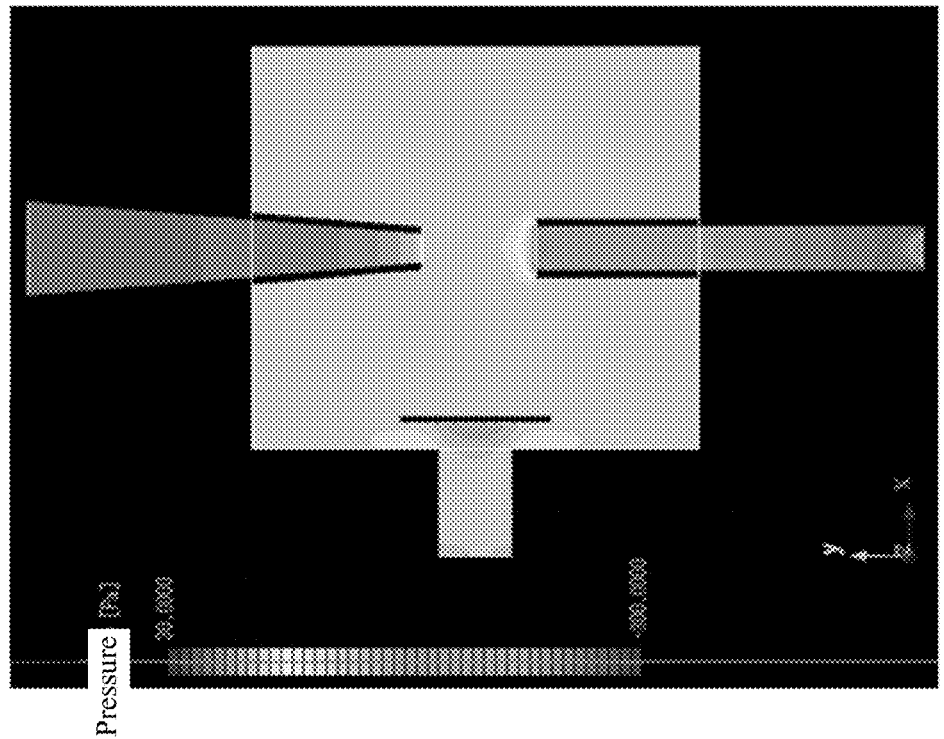
FIG. 11 is a simulation result illustrating the distribution of pressures within the chamber of the particle detecting device in a case wherein a flow rectifying member is provided.

In the Another Example, the rectifying member 62 is a plate, having no spaces, disposed facing the opening of the pressurizing fluid pipe 50 that is connected to the chamber 10. FIG. 9 shows the distribution of particles within the chamber of the particle detecting device that has the plate with no spaces that is disposed facing the opening of the pressurizing fluid pipe, FIG. 10 shows the distribution of the flow speeds, and FIG. 11 shows the distribution of the pressures. The distributions illustrated in FIG. 9 through FIG. 11 are the results of simulations. Because the rectifying member is provided, the particles are discharged from the discharge nozzle, as illustrated in FIG. 9. Moreover, as illustrated in FIG. 10, the pressurizing fluid is prevented from arriving at between the injection nozzle and the discharge nozzle with the flow speed still high. Furthermore, as illustrated in FIG. 11, in the vicinity of between the injection nozzle and the discharge nozzle, the pressure distribution is symmetrical.

Figure 12:
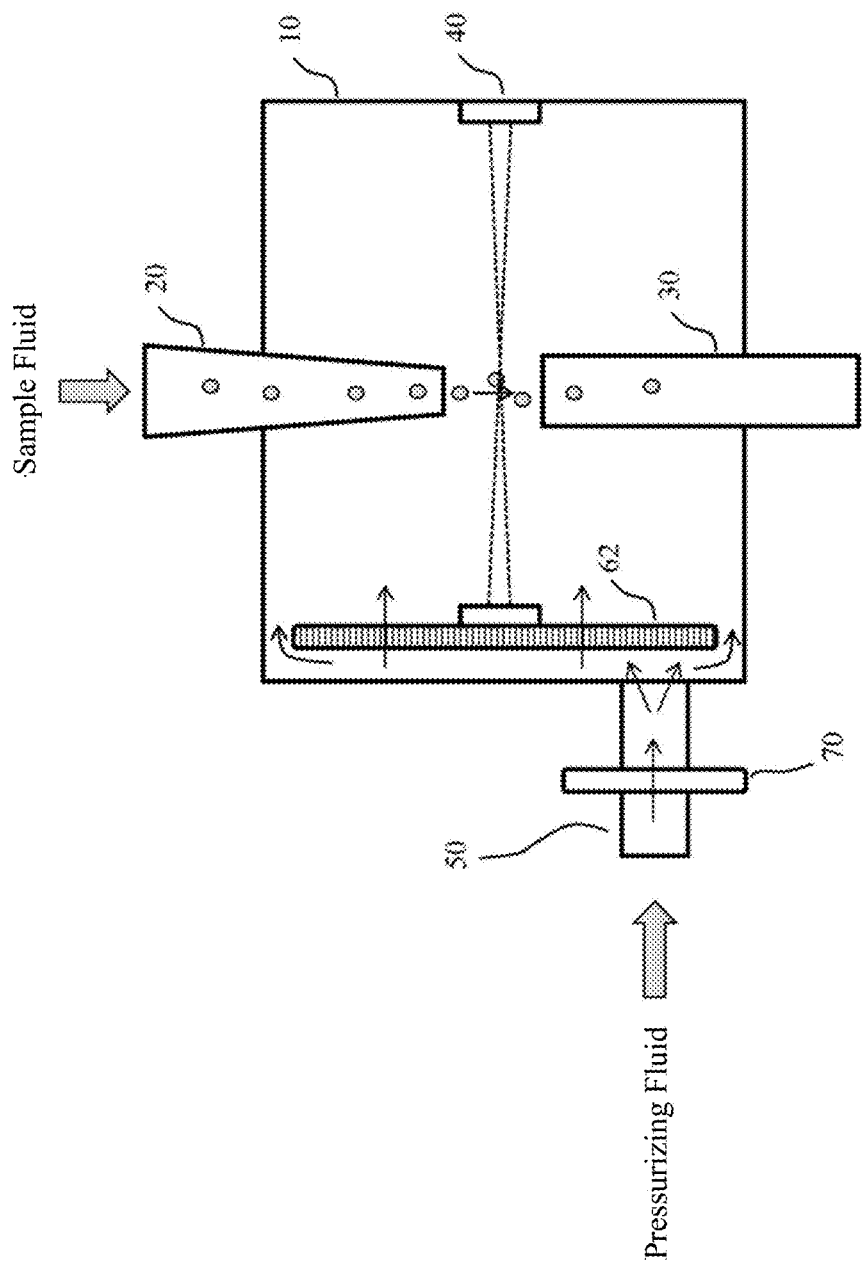
FIG. 12 is a schematic diagram of a particle detecting device as set forth in the Another Example according to the present disclosure.

Conversely, in the Another Example, the rectifying member 62, as illustrated in FIG. 12, may be a mesh, a filter, or a porous member, disposed facing the opening of the pressurizing fluid pipe 50 that is connected to the chamber 10. The mesh, filter, or porous member may be the same as that would which was used in the Another Example. The rectifying member 62 is disposed between the sidewall, wherein the opening of the pressurizing fluid pipe 50 is provided, and the injection nozzle 20 and discharge nozzle 30. Moreover, the rectifying member 62 is disposed essentially parallel to the direction of flow of the sample fluid between the injection nozzle 20 and the discharge nozzle 30. The provision of the rectifying member 62 makes it possible to prevent the pressurizing fluid that flows into the chamber 10 from the pressurizing fluid pipe 50 from disrupting asymmetrically the flow speed distribution of the fluid between the injection nozzle 20 and the discharge nozzle 30 that has been rectified in the axial direction.

If the rectifying member 62 is a mesh, a filter, or a porous member, then the sizes of the diameters of the individual spaces in the rectifying member 62 are smaller than, for example, the diameter of the opening of the injection nozzle 20. Moreover, for example, the sum of the areas of the openings in the rectifying member 62 is larger than the cross-sectional area of the pressurizing fluid pipe 50. Having the sum of the areas of openings in the rectifying member 62 be larger than the cross-sectional area of the pipe 50 of the pressurizing fluid makes it possible to distribute the pressure of the pressurizing fluid uniformly within the chamber 10. Furthermore, having the sum of the areas of the openings that are provided in the rectifying member 62 be larger than the cross-sectional area of the pressurizing fluid pipe 50 makes it possible to reduce the speed of flow of the fluid that passes through the rectifying member 62, when compared to the speed of the fluid within the pressurizing fluid pipe 50.

Figure 13:
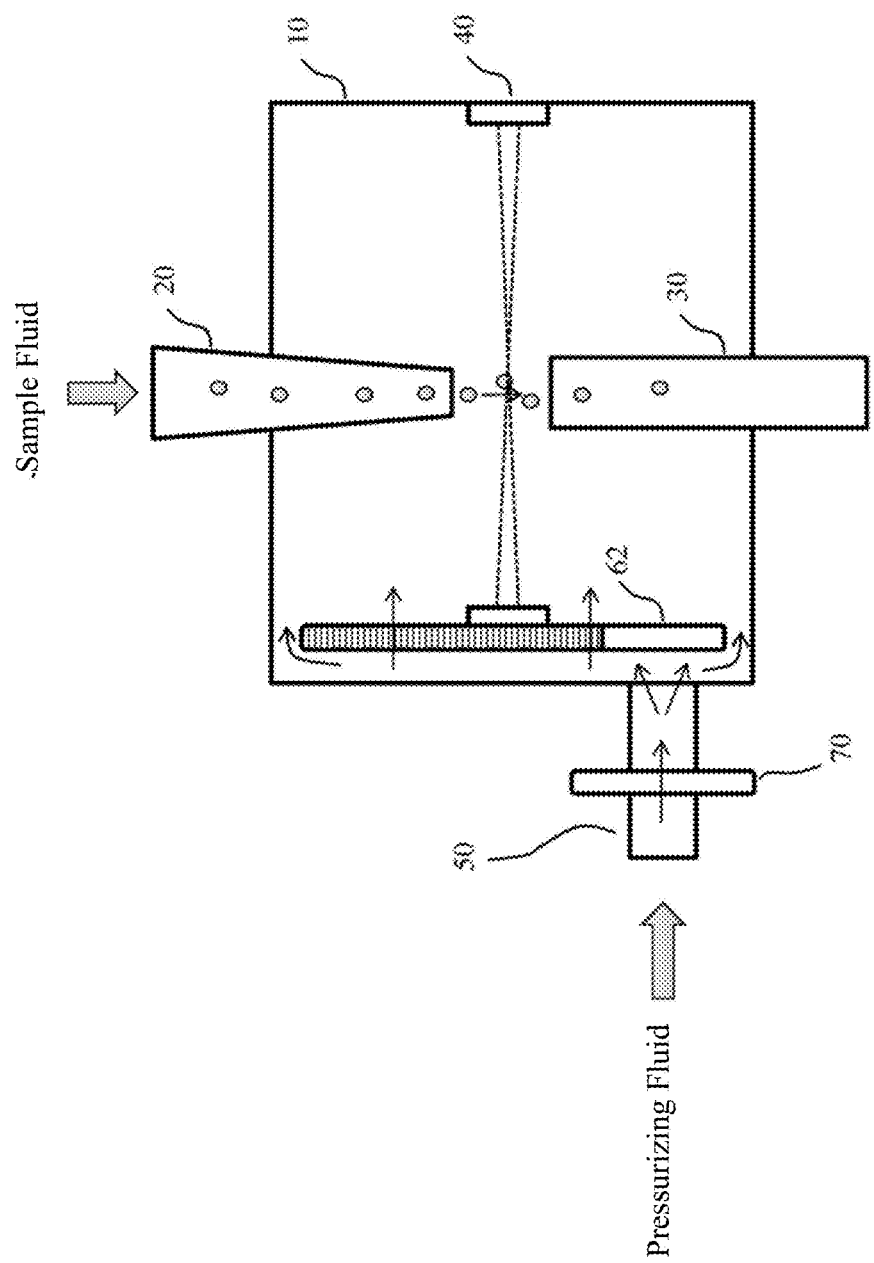
FIG. 13 is a schematic diagram of a particle detecting device as set forth in the Another Example according to the present disclosure.

Moreover, as illustrated in FIG. 13, for example, the rectifying member 62 may have a part wherein there are no spaces and a part that has spaces, made from a mesh, a filter, or a porous member. In this case, the part of the rectifying member 62 that has no spaces may, for example, face the opening of the pressurizing fluid pipe 50. Note that having the part that has spaces, being made from a mesh, a filter, or a porous member, be large, except for the part that faces the opening of the pressurizing fluid pipe 50 directly, tends to improve the rectifying effect through distributing the pressure of the pressurizing fluid uniformly.

In the Another Example, at least a portion of the detecting mechanism 40, such as the light source, photodetecting element, or the like, of the detecting mechanism 40, may be disposed in the rectifying member 62. As illustrated in FIG. 12 and FIG. 13, if at least a portion of the rectifying member 62 is a mesh, a filter, or a porous member, the light source, photodetecting element, or the like, of the detecting mechanism 40, which is disposed in a position that is perpendicular to the flow of the sample fluid between the injection nozzle 20 and the discharge nozzle 30, can prevent the pressurizing fluid from colliding with the flow of the sample fluid between the injection nozzle 20 and the discharge nozzle 30.

YET ANOTHER EXAMPLE

Figure 14:
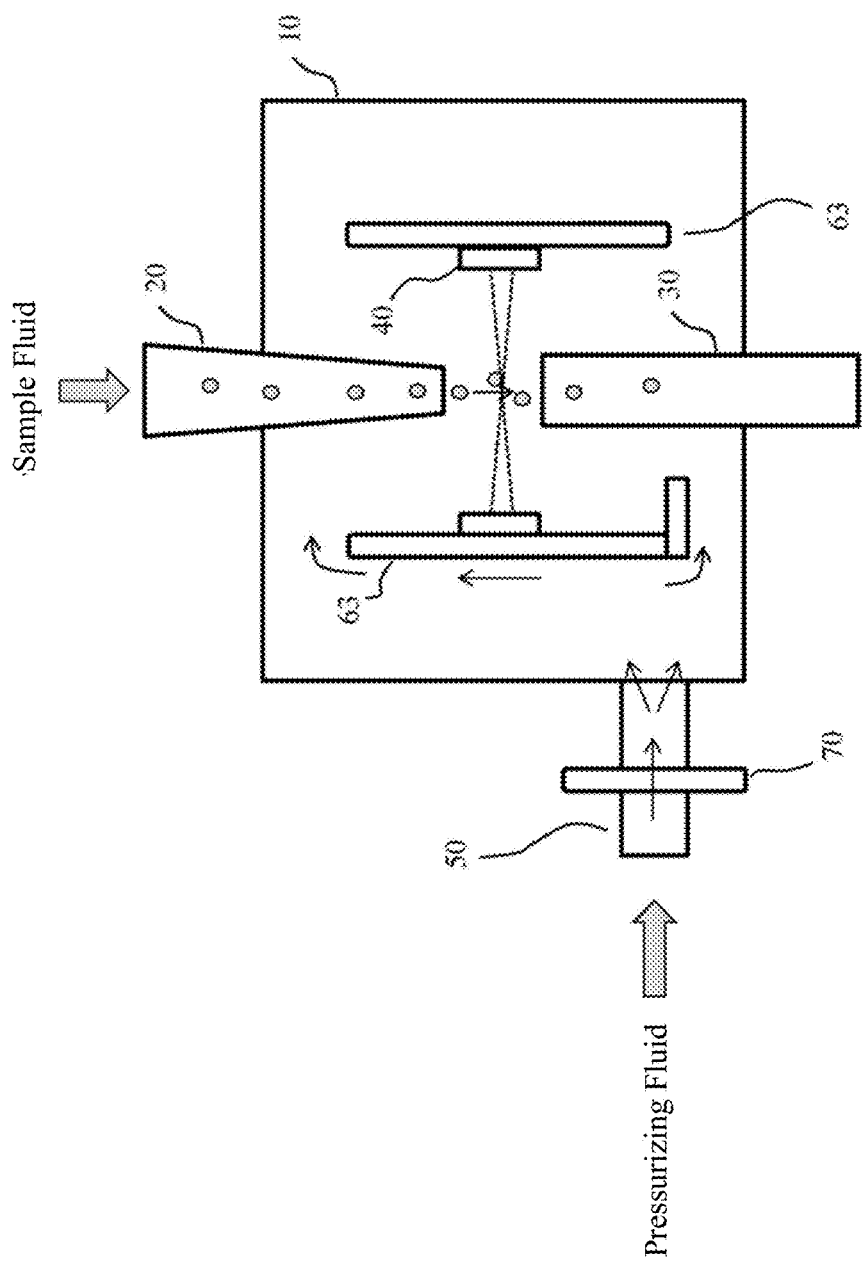
FIG. 14 is a schematic diagram of a particle detecting device as set forth in Yet Another Example according to the present disclosure.
Figure 15:
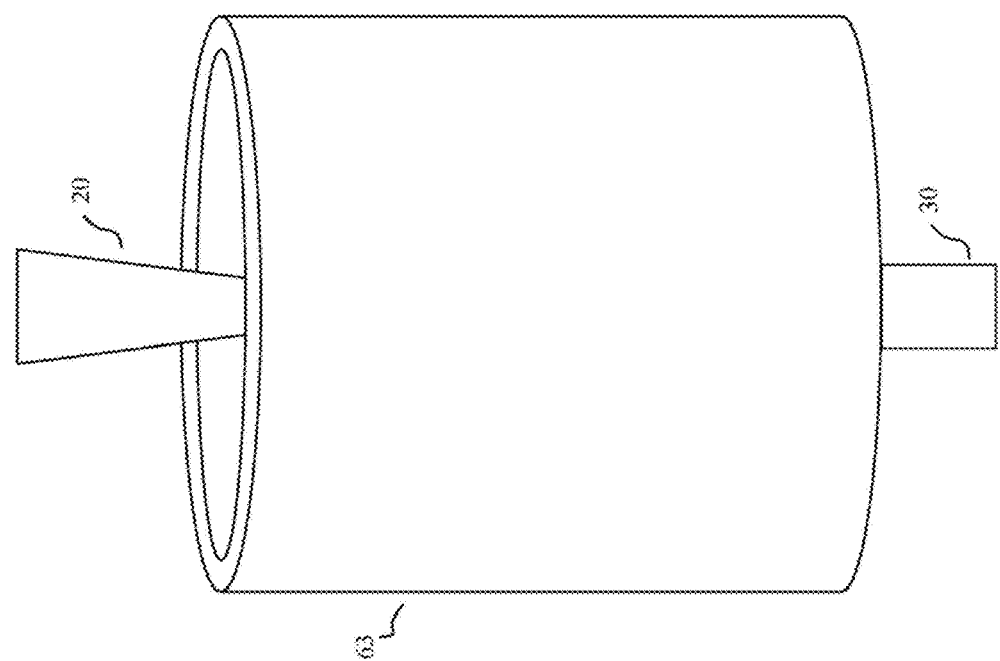
FIG. 15 is a schematic diagram of a flow rectifying member in the particle detecting device as set forth in the Yet Another Example according to the present disclosure.

In a particle detecting device according to Yet Another Example, as illustrated in FIG. 14 and FIG. 15, the end of the pressurizing fluid pipe 50 is connected to an outer diameter part of an opening that is provided in a side wall of the chamber 10. The pressurizing fluid that is supplied from the pressurizing fluid pipe 50 is supplied into the chamber 10 from the opening that is provided in the sidewall of the chamber 10. For example, the sidewall of the chamber 10 wherein the opening through which the pressurizing fluid passes is provided is essentially parallel to the direction of flow of the sample fluid between the injection nozzle 20 and the discharge nozzle 30.

Figure 16:
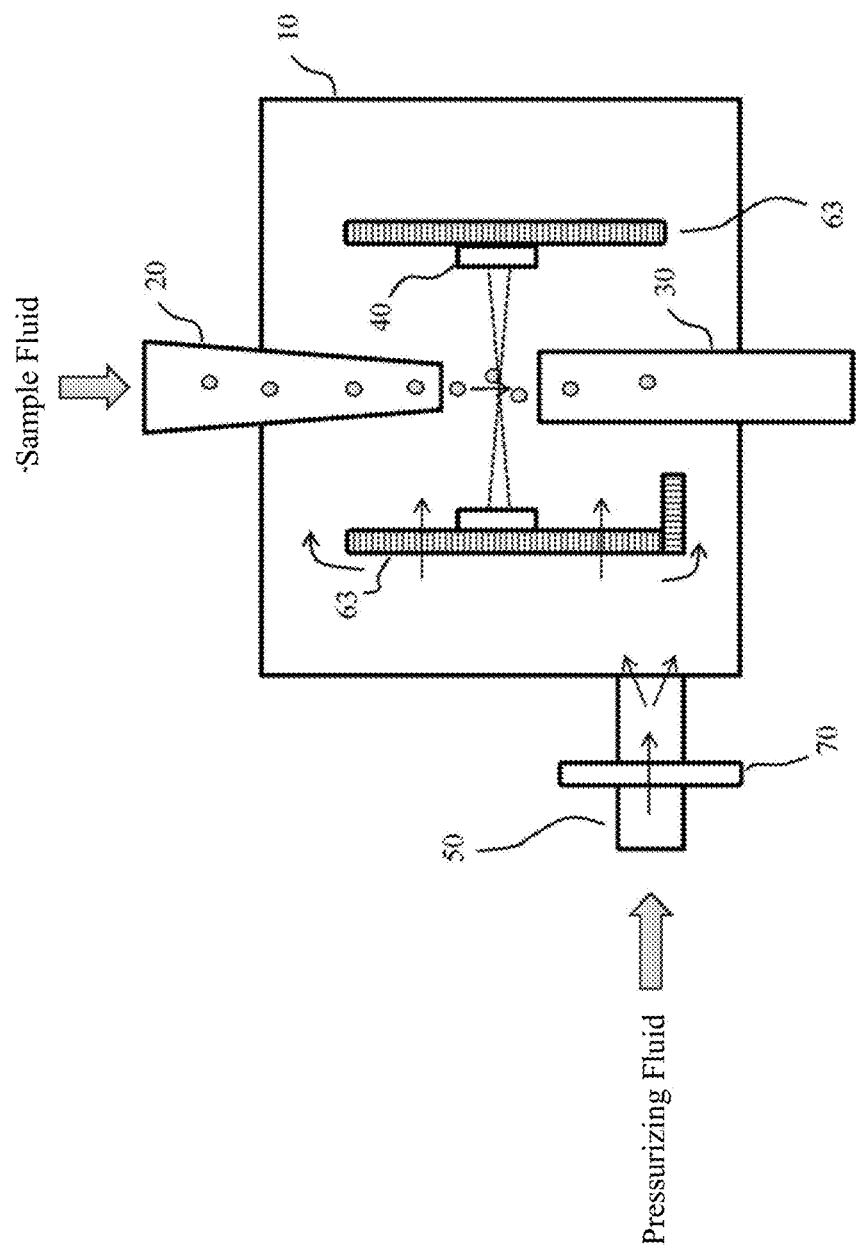
FIG. 16 is a schematic diagram of a particle detecting device as set forth in the Yet Another Example according to the present disclosure.

In the Yet Another Example, the rectifying member 63 is a tubular member covering at least between the injection nozzle 20 and the discharge nozzle 30. The rectifying member 63 may be a member with no spaces, or, as illustrated in FIG. 16, may be a mesh, a filter, or a porous membrane. The mesh, filter, or porous member may be the same as that would which was used in the Example. In the Yet Another Example, the shape of the rectifying member 63 is arbitrary, insofar as it is tubular, and, for example, may be cylindrical, or may be a square tube shape. The provision of the rectifying member 63 makes it possible to prevent the pressurizing fluid that flows into the chamber 10 from the pressurizing fluid pipe 50 from disrupting asymmetrically the flow speed distribution of the fluid between the injection nozzle 20 and the discharge nozzle 30 that has been rectified in the axial direction.

If the rectifying member 63 is a mesh, a filter, or a porous member, then the sizes of the diameters of the individual spaces in the rectifying member 63 are smaller than, for example, the diameter of the opening of the injection nozzle 20. Moreover, for example, the sum of the areas of the openings in the rectifying member 63 is larger than the cross-sectional area of the pressurizing fluid pipe 50. Having the sum of the areas of openings in the rectifying member 63 be larger than the cross-sectional area of the pipe 50 of the pressurizing fluid makes it possible to distribute the pressure of the pressurizing fluid uniformly within the chamber 10. Furthermore, having the sum of the areas of the openings that are provided in the rectifying member 63 be larger than the cross-sectional area of the pressurizing fluid pipe 50 makes it possible to reduce the speed of flow of the fluid that passes through the rectifying member 63, when compared to the speed of the fluid within the pressurizing fluid pipe 50.

Figure 17:
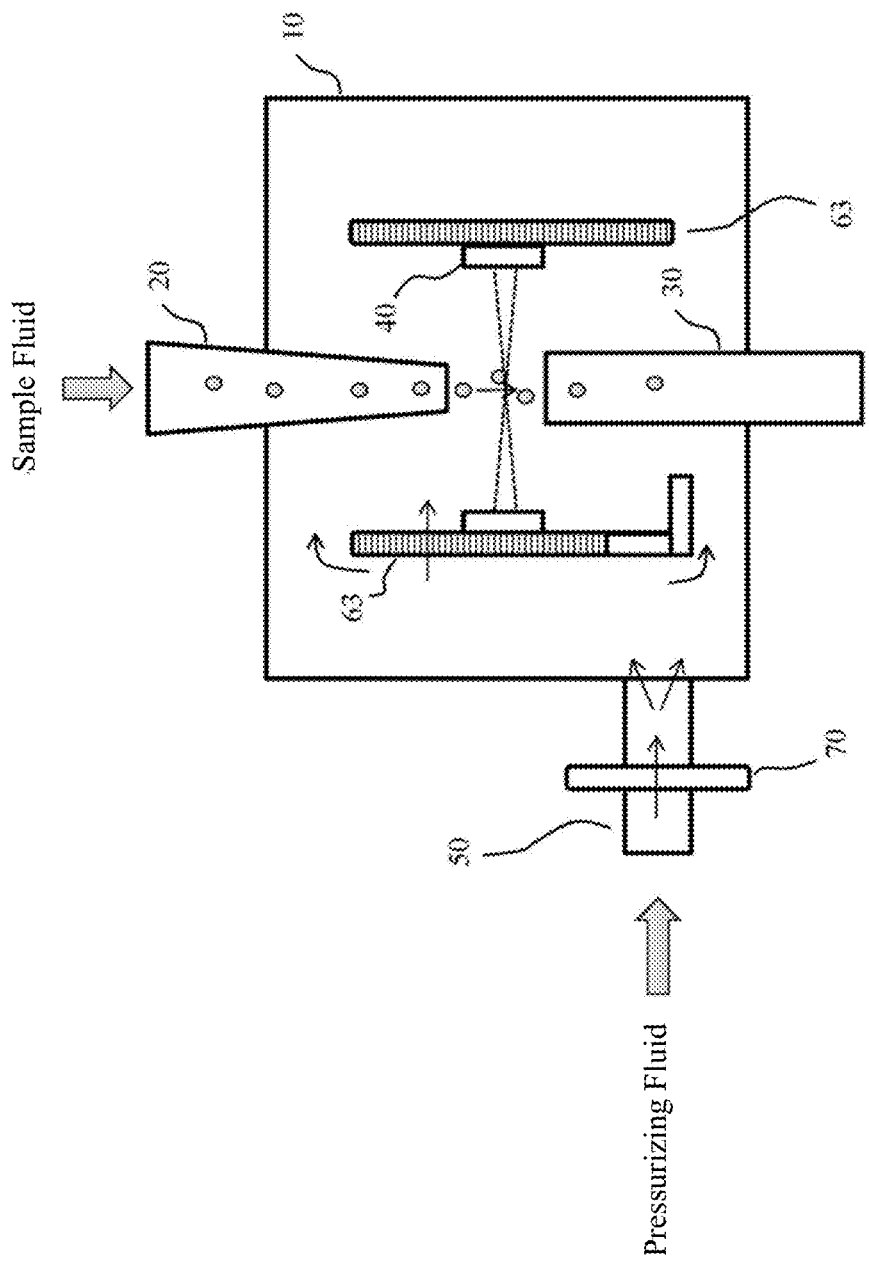
FIG. 17 is a schematic diagram of a particle detecting device as set forth in the Yet Another Example according to the present disclosure.

Moreover, as illustrated in FIG. 17, for example, the rectifying member 63 may have a part wherein there are no spaces and a part made from a mesh, a filter, or a porous member. In this case, the part of the rectifying member 63 that has no spaces may, for example, face the opening of the pressurizing fluid pipe 50. Note that having the part made from a mesh, a filter, or a porous member be large, except for the part that faces the opening of the pressurizing fluid pipe 50 directly, calms the flow of the pressurizing fluid, and tends to improve the rectifying effect through distributing the pressure of the pressurizing fluid uniformly.

In the Yet Another Example, at least a portion of the detecting mechanism 40 may be disposed in the rectifying member 63. As illustrated in FIG. 16 and FIG. 17, if at least a portion of the rectifying member 63 is a mesh, a filter, or a porous member, the light source, photodetecting element, or the like, of the detecting mechanism 40, which is disposed in a position that is perpendicular to the flow of the sample fluid between the injection nozzle 20 and the discharge nozzle 30, can prevent the pressurizing fluid from colliding with the flow of the sample fluid between the injection nozzle 20 and the discharge nozzle 30.

FURTHER EXAMPLE

Figure 18:
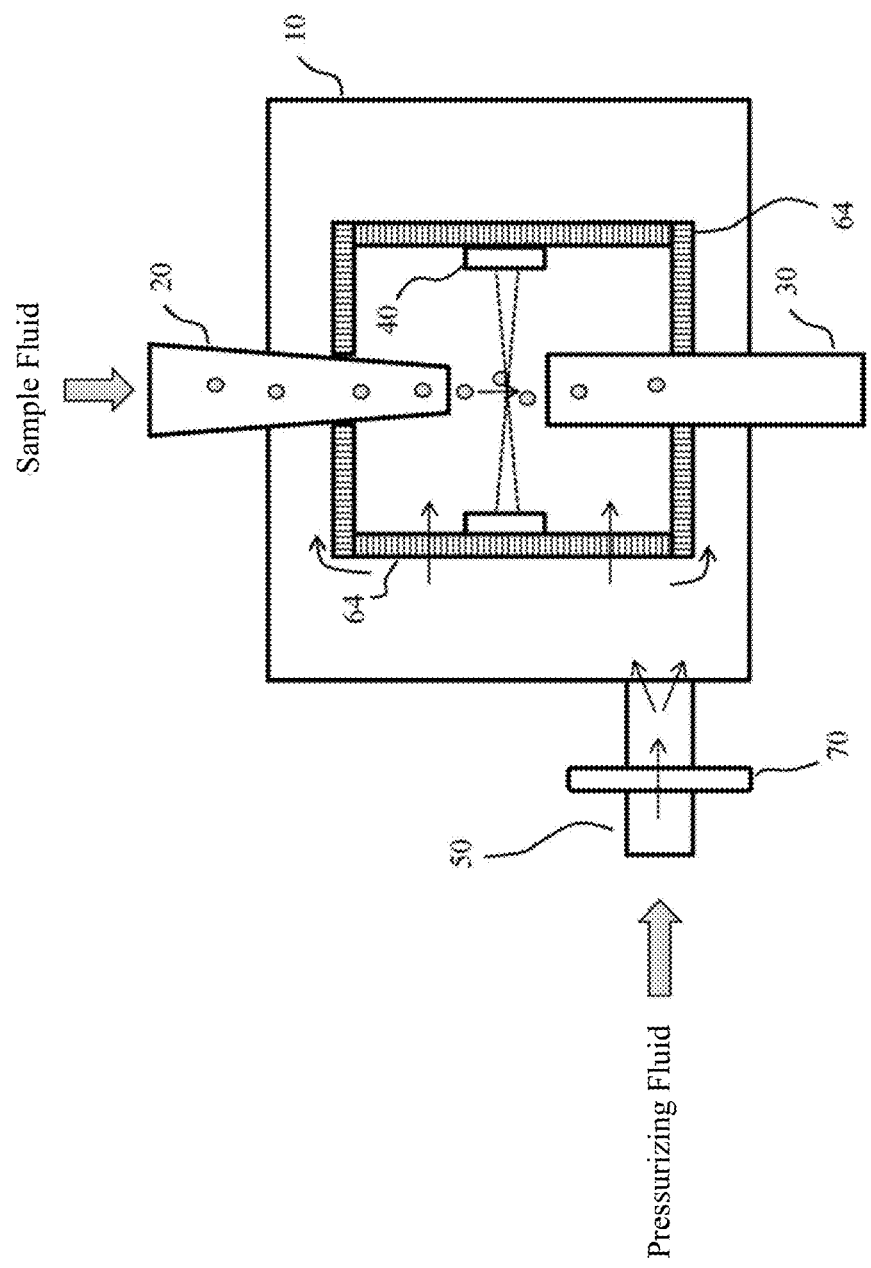
FIG. 18 is a schematic diagram of a particle detecting device as set forth in Further Example according to the present disclosure.

In a particle detecting device according to Further Example, as illustrated in FIG. 18, the end of the pressurizing fluid pipe 50 is connected to an outer diameter part of an opening that is provided in a side wall of the chamber 10. The pressurizing fluid that is supplied from the pressurizing fluid pipe 50 is supplied into the chamber 10 from the opening that is provided in the sidewall of the chamber 10. For example, the sidewall of the chamber 10 wherein the opening through which the pressurizing fluid passes is provided is essentially parallel to the direction of flow of the sample fluid between the injection nozzle 20 and the discharge nozzle 30.

In the Further Example, the rectifying member 64 is a second chamber disposed within the chamber 10, where the injection nozzle 20 and the discharge nozzle 30 face each other within the second chamber. The rectifying member 64 is made from, for example, a mesh, a filter, or a porous member. The mesh, filter, or porous member may be the same as that would which was used in the Example. In the Further Example, the shape of the rectifying member 64 is arbitrary, and may be, for example, a cube, a rectangular parallelepiped, a sphere, or an elliptical spheroid. The sizes of the diameters of the individual spaces in the rectifying member 64 are smaller than, for example, the diameter of the opening of the injection nozzle 20. Moreover, for example, the sum of the areas of the openings in the rectifying member 64 is larger than the cross-sectional area of the pressurizing fluid pipe 50. Having the sum of the areas of openings in the rectifying member 64 be larger than the cross-sectional area of the pipe 50 of the pressurizing fluid makes it possible to distribute the pressure of the pressurizing fluid uniformly within the chamber 10, even when the flow rate of the pressurizing fluid is large.

Figure 19:
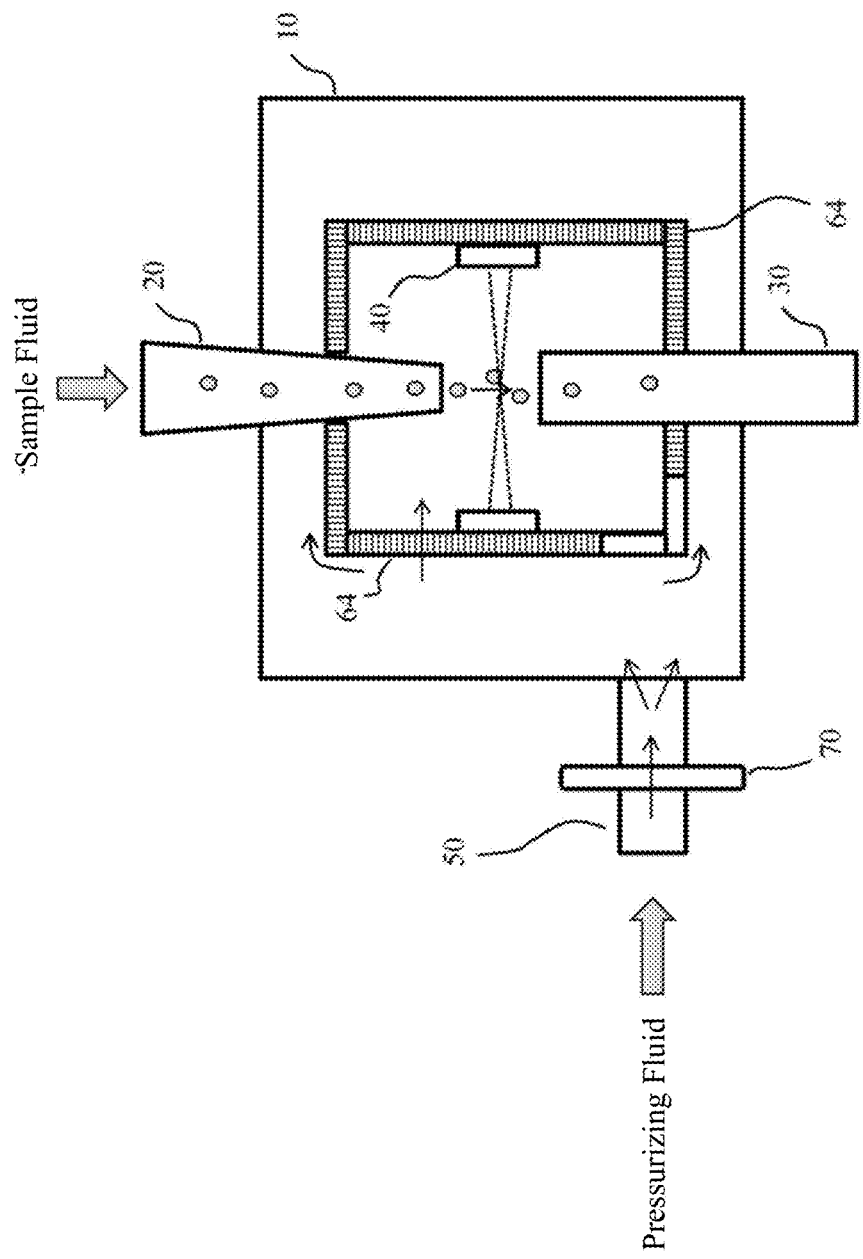
FIG. 19 is a schematic diagram of a particle detecting device as set forth in the Further Example according to the present disclosure.
Figure 20:
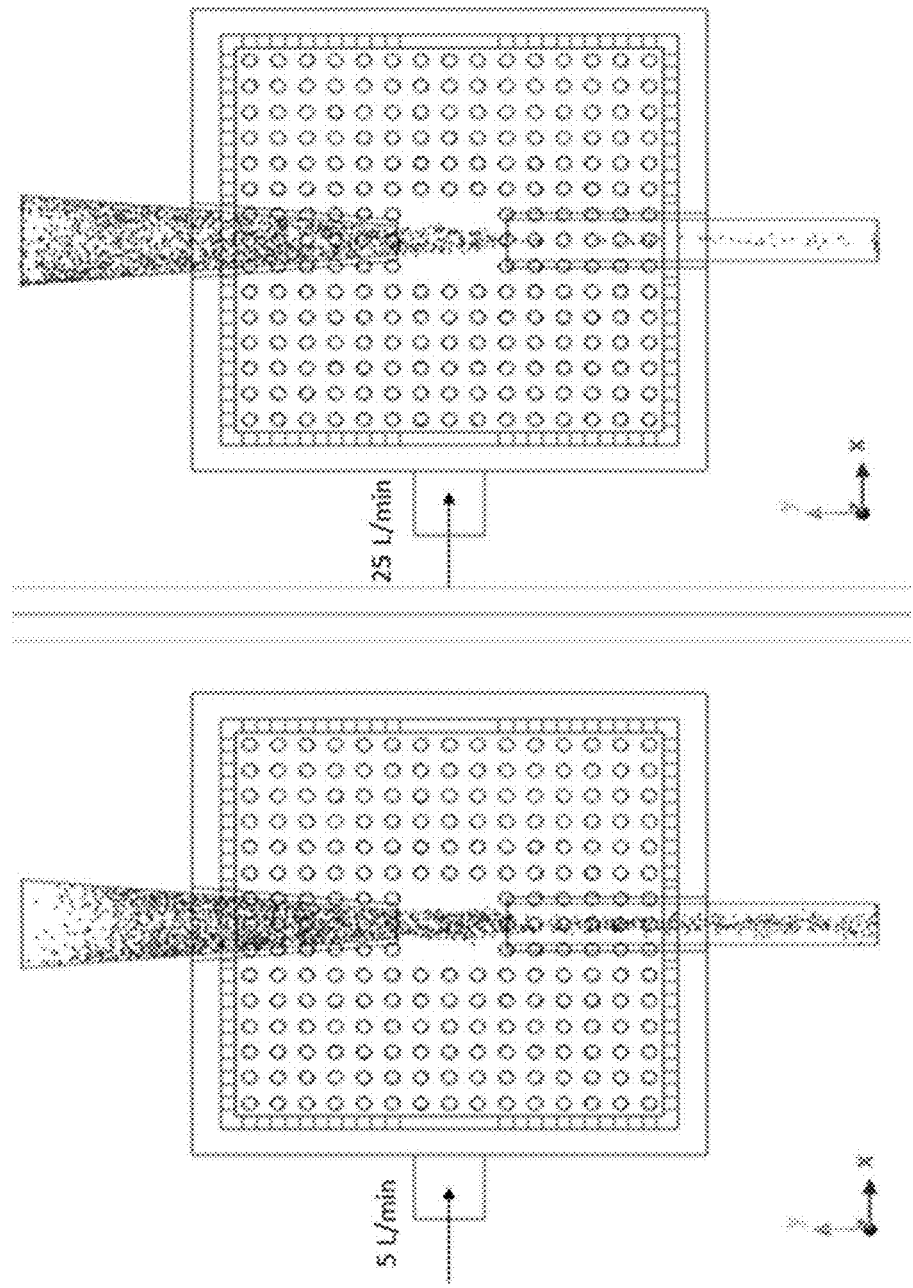
FIG. 20 is a simulation result illustrating the distribution of particles within the chamber of the particle detecting device in a case wherein a second chamber is provided.
Figure 21:
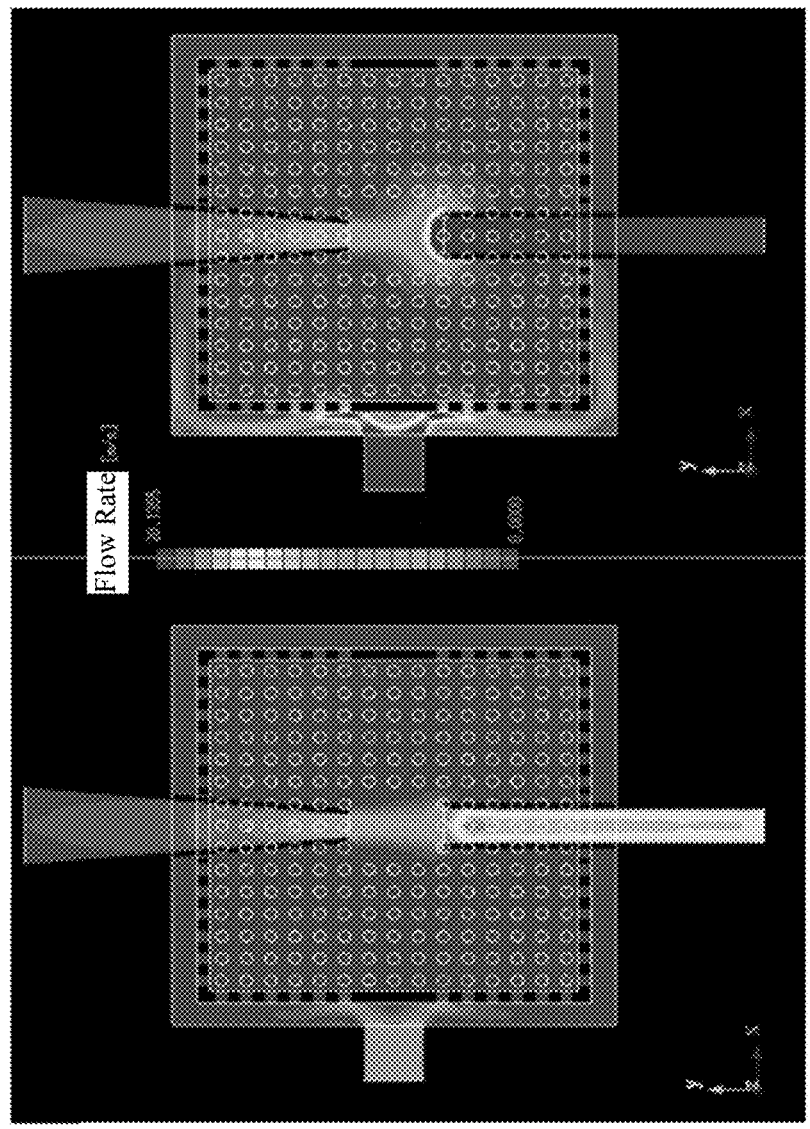
FIG. 21 is a simulation result illustrating the distribution of flow speeds within the chamber of the particle detecting device in a case wherein a second chamber is provided.
Figure 22:
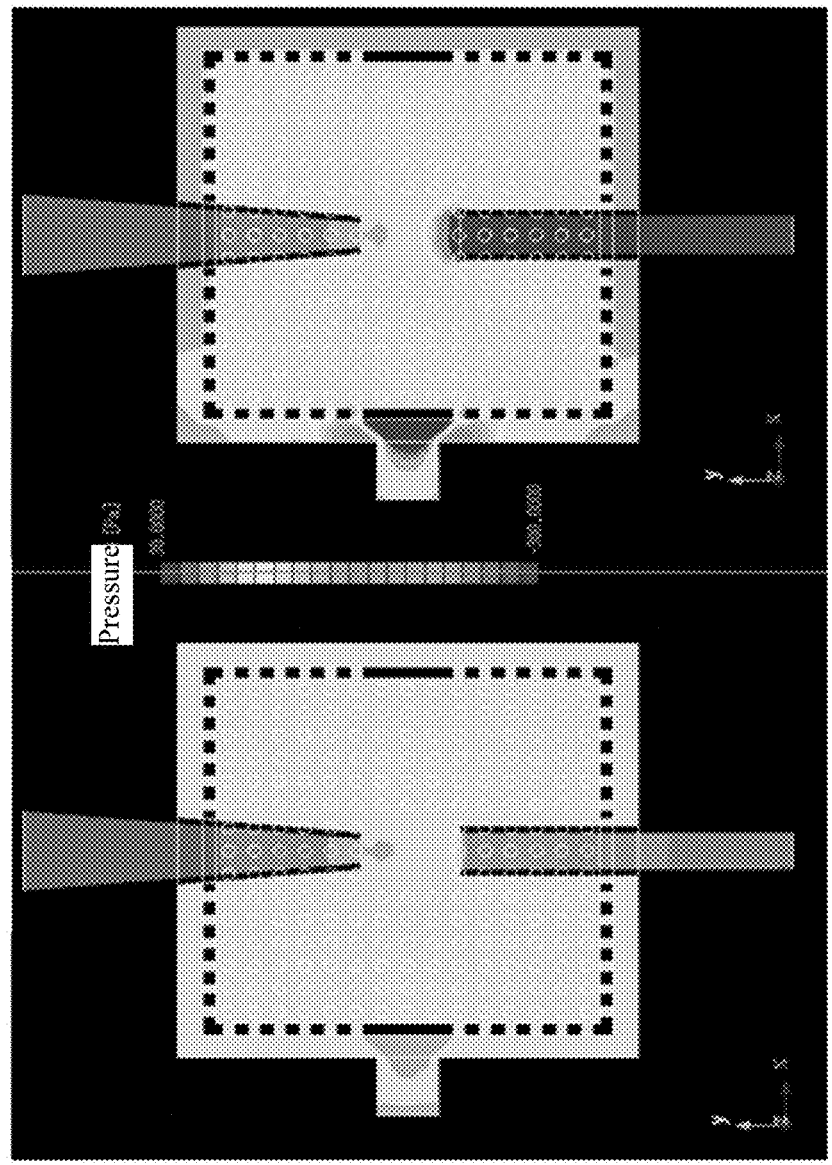
FIG. 22 is a simulation result illustrating the distribution of pressures within the chamber of the particle detecting device in a case wherein a second chamber is provided.

Moreover, as illustrated in FIG. 19, for example, the rectifying member 64 may have a part wherein there are no spaces and a part having spaces, made from a mesh, a filter, or a porous member. In this case, the part of the rectifying member 64 that has no spaces may, for example, face the opening of the pressurizing fluid pipe 50. Note that having the part that has spaces, being made from a mesh, a filter, or a porous member, be large, except for the part that faces the opening of the pressurizing fluid pipe 50 directly, tends to improve the rectifying effect through distributing the pressure of the pressurizing fluid uniformly, even when the flow rate of the pressurizing fluid is large. FIG. 20 shows the distribution of particles within the chamber of a particle detecting device that has a second chamber that has spaces at other than the part that faces the pressurizing fluid pipe, FIG. 21 shows the distribution of the flow speeds, and FIG. 22 shows the distribution of the pressures. The distributions illustrated in FIG. 20 through FIG. 22 are the results of simulations. Because the second chamber is provided, the particles are discharged from the discharge nozzle, as illustrated in FIG. 20. Moreover, as illustrated in FIG. 21, the pressurizing fluid is prevented from arriving at between the injection nozzle and the discharge nozzle with the flow speed still high. Furthermore, as illustrated in FIG. 22, in the vicinity of between the injection nozzle and the discharge nozzle, the pressure distribution is symmetrical. This effect is still present even when the pressure of the pressurizing fluid is increased.

Figure 23:
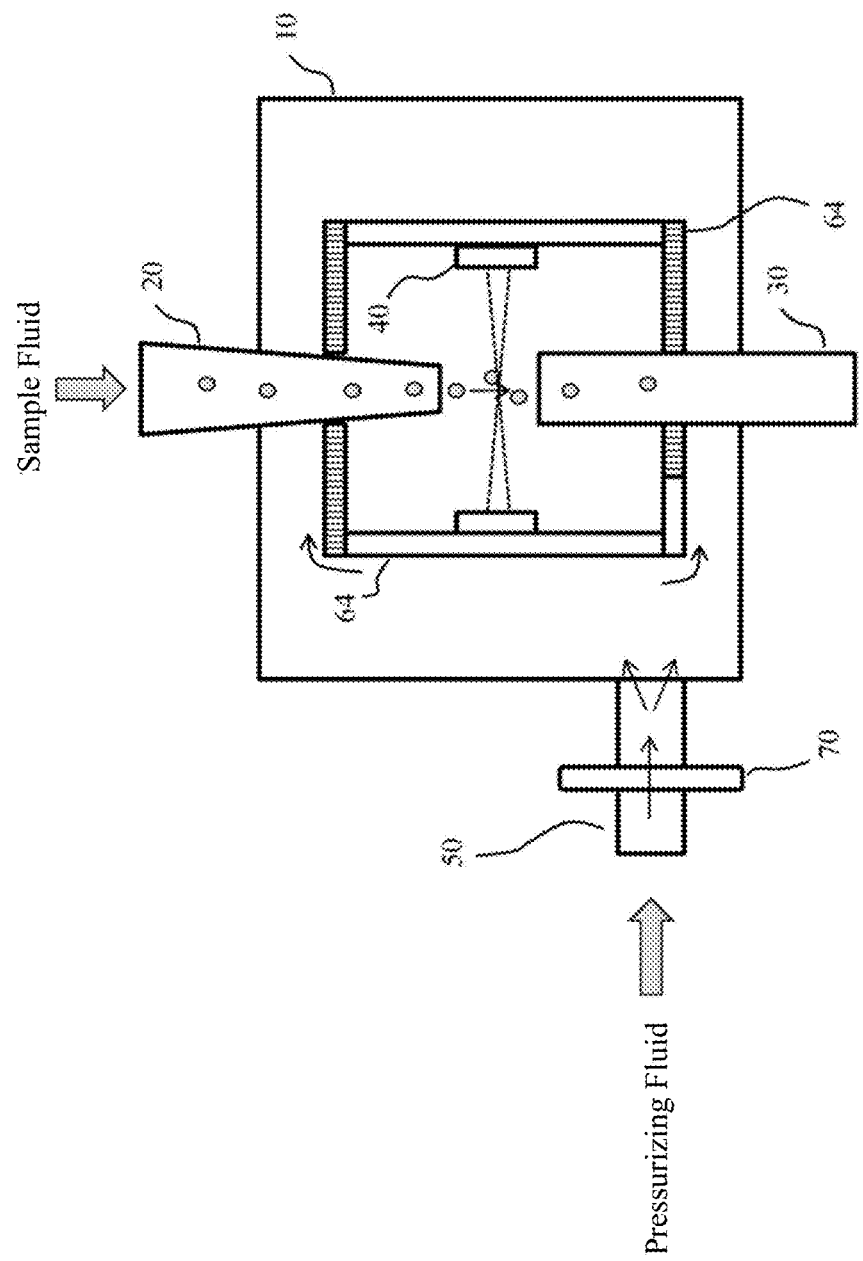
FIG. 23 is a schematic diagram of a particle detecting device as set forth in the Further Example according to the present disclosure.

Conversely, the rectifying member 64, as illustrated in FIG. 23, may be formed from a member wherein there are no spaces in the side face that is essentially parallel to the direction of flow of the sample fluid between the injection nozzle 20 and the discharge nozzle 30, with the top face, through which the injection nozzle 20 passes, and the bottom face, through which the discharge nozzle 30 passes, formed from meshes, filters, or porous members. Note that having the part that has spaces, made from a mesh, a filter, or a porous member, be large, except for the part that faces the opening of the pressurizing fluid pipe 50 directly, calms the flow of the pressurizing fluid, and tends to improve the rectifying effect through distributing the pressure of the pressurizing fluid uniformly, even when the flow rate of the pressurizing fluid is large.

In the Further Example, at least a portion of the detecting mechanism 40 may be disposed in the rectifying member 64. As illustrated in FIG. 18 and FIG. 19, if at least a portion of the rectifying member 64 is a mesh, a filter, or a porous member, the light source, photodetecting element, or the like, of the detecting mechanism 40, which is disposed in a position that is perpendicular to the flow of the sample fluid between the injection nozzle 20 and the discharge nozzle 30, can prevent the pressurizing fluid from colliding with the flow of the sample fluid between the injection nozzle 20 and the discharge nozzle 30.

The provision of the rectifying member 64 makes it possible to prevent the pressurizing fluid that flows into the chamber 10 from the pressurizing fluid pipe 50 from disrupting asymmetrically the flow speed distribution of the fluid between the injection nozzle 20 and the discharge nozzle 30 that has been rectified in the axial direction. Moreover, in the Further Example, the rectifying member 64 is a second chamber that is disposed in the chamber 10, and thus the particles are sealed within the second chamber, making it possible to prevent the pressurizing fluid pipe 50, and the like, from becoming contaminated with particles. Moreover, this also makes it possible to avoid the risk of contamination through the incursion, into the second chamber, of particles included in the pressurizing fluid even if the pressurizing fluid filter 70 were to rupture unexpectedly. Furthermore, if the diameters of the holes provided in the second chamber are smaller than the sizes of the particles, the pressurizing fluid filter 70 can be eliminated.

OTHER EXAMPLES

While there are descriptions of examples as set forth above, the descriptions and drawings that form a portion of the disclosure are not to be understood to limit the present disclosure. A variety of alternate examples and operating technologies should be obvious to those skilled in the art. For example, while preferably if no rectifying member 61 through 64 is provided, the opening of the pressurizing fluid pipe 50 is further than the positions at which the injection nozzle 20 in the discharge nozzle 30 face each other, the provision of the rectifying member 61 through 64 enables the pressurizing fluid pipe 50 to be connected at an arbitrary position within the chamber 10. In this way, the present disclosure should be understood to include a variety of examples, and the like, not set forth herein.

The invention claimed is:
1. A particle detecting device comprising:
a chamber;

an injection nozzle provided within the chamber;
a discharge nozzle that is disposed within the chamber, opposing the injection nozzle;
a detecting mechanism that illuminates a sample fluid that is sprayed from the injection nozzle and detects a particle included in the sample fluid;
a pressurizing fluid pipe, connected to the chamber, for supplying a pressurizing fluid for pressurizing an interior of the chamber; and
a rectifying member comprising a second chamber disposed within the chamber, wherein the injection nozzle and the discharge nozzle face each other within the second chamber, and wherein the rectifying member rectifies the pressurizing fluid so that a flow speed distribution of a fluid between the injection nozzle and the discharge nozzle, rectified in an axial direction, is symmetrical in respect to the axial direction.

* * * * *